(12) United States Patent
Gillman et al.

(10) Patent No.: US 6,930,100 B2
(45) Date of Patent: Aug. 16, 2005

(54) PHOSPHATE PRODRUGS OF FLUOROXINDOLES

(75) Inventors: Kevin W. Gillman, Madison, CT (US); Piyasena Hewawasa, Middletown, CT (US); William D. Schmitz, Cheshire, CT (US); Omar D. Lopez, Wallingford, CT (US); John E. Starrett, Middletown, CT (US); David P. Provencal, Cromwell, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/393,031

(22) Filed: Mar. 20, 2003

(65) Prior Publication Data

US 2003/0195169 A1 Oct. 16, 2003

Related U.S. Application Data

(60) Provisional application No. 60/366,010, filed on Mar. 20, 2002.

(51) Int. Cl.[7] .................. A61K 31/675; C07F 9/572
(52) U.S. Cl. .......................... 514/80; 548/414
(58) Field of Search .................. 514/80, 81; 548/414

(56) References Cited

U.S. PATENT DOCUMENTS

| 5,187,173 A | 2/1993 | Desai et al. |
| 5,602,169 A | 2/1997 | Hewawasam et al. |
| 5,939,405 A | 8/1999 | Starrett et al. |

FOREIGN PATENT DOCUMENTS

| WO | WO 93/08800 | 5/1993 |
| WO | WO 99/33846 | 8/1999 |

OTHER PUBLICATIONS

Ahmed, F. et al., *Br. J. Pharmacol.*, 83, pp. 227–233 (1984).
Baró, I., and Escande, D., *Pflügers Archiv.*, 414 (Suppl. 1), pp. S168–S170 (1989).
Cook, N.S., *Trends in Pharmacol. Sciences*, 9, pp. 21–28 (1988).
Gribkoff, et al., *Nature Medicine*, 7, 471–477 (2001).
Koh, D–S., et al., *Neuroscience Lett.*, 165, pp. 167–170 (1994).
Quast, U. and Cook, N.S., *Trends in Pharmacol. Sciences*, 10, pp. 431–435 (1989).
Singer, J. J. and Walsh, J. V., *Pflügers Archiv.*, 408, pp. 98–111 (1987).
Trivedi, et al. in *Biochemical and Biophysical Research Communications*, 213, No. 2, pp. 404–409 (1995).
Varia, S.A., et al., *J. Pharm. Sci.* 73, pp. 1068–1073 (1984).

*Primary Examiner*—Fiona T. Powers
(74) *Attorney, Agent, or Firm*—Aldo A. Algieri

(57) ABSTRACT

The present invention provides novel phosphate derivatives having the general Formula I

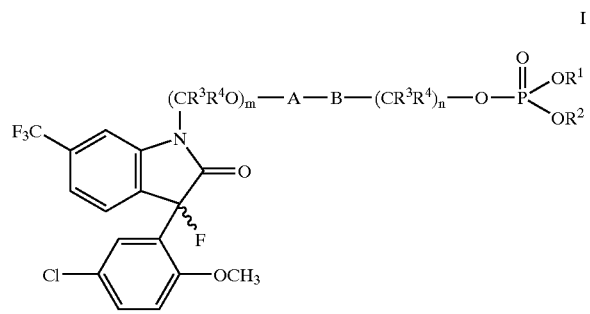

wherein the wavy bond (∿) represents the racemate, the (R)-enantiomer or the (S)-enantiomer and A, B, $R^1$, $R^2$, $R^3$, $R^4$, m and n are as defined herein, or a nontoxic pharmaceutically acceptable salt or solvate thereof and are useful in the treatment of disorders which are responsive to the opening of potassium channels.

10 Claims, No Drawings

PHOSPHATE PRODRUGS OF FLUOROXINDOLES

CROSS REFERENCE TO RELATED APPLICATION

This is a non-provisional application which claims the benefit of provisional application U.S. Ser. No. 60/366,010 filed Mar. 20, 2002.

FIELD OF THE INVENTION

The present invention is directed to novel phosphate derivatives of a fluorooxindole compound which is a modulator of the large-conductance calcium-activated potassium (BK) channels and, therefore, useful in the protection of neuronal cells and diseases arising from dysfunction of cellular membrane polarization and conductance. The present invention also provides a method of treatment with the novel substituted fluorooxindole derivatives and to pharmaceutical compositions thereof.

BACKGROUND OF THE INVENTION

Stroke is presently recognized as the third leading cause of adult disability and death in the United States and Europe. In the past decade, several therapeutic approaches for the minimization of stroke-related brain damage have been pursued including inhibitors of AMPA/kainate, N-methyl-D-aspartate (NMDA) and adenosine reuptake inhibitors. It is the object of the present invention to provide novel compounds that will modulate potassium channels, in particular, large-conductance calcium-activated potassium (BK) channels which will be useful in reducing neuronal damage during ischemic conditions of a stroke episode.

Potassium channels play a key role in regulation of cell membrane potential and modulation of cell excitability. Potassium channels are themselves regulated by voltage, cell metabolism, calcium ion and receptor mediated processes. [Cook, N. S., *Trends in Pharmacol. Sciences,* 9, pp. 21–28 (1988); and Quast, U. and Cook, N. S., *Trends in Pharmacol, Sciences,* 10, pp. 431–435 (1989)]. Calcium-activated potassium ($K_{Ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (BK)>150 pS; intermediate conductance 50–150 pS; small conductance<50 pS. ("pS" stands for picosiemen, a unit of electrical conductance.) Large-conductance calcium-activated potassium (BK) channels are present in many excitable cells including neurons, cardiac cells and various types of smooth muscle cells. [Singer, J. J. and Walsh, J. V., *Pflügers Archiv.,* 408, pp. 98–111 (1987); Baró, I., and Escande, D., *Pflügers Archiv.,* 414 (Suppl. 1), pp. S168–S170 (1989); and Ahmed, F. et al., *Br. J. Pharmacol.,* 83, pp. 227–233 (1984)].

Potassium ions play a dominant role in controlling the resting membrane potential in most excitable cells and in maintaining the transmembrane voltage near the $K^+$ equilibrium potential ($E_k$) of about –90 mV. It has been shown that opening of potassium channels shifts the cell membrane potential towards the equilibrium potassium membrane potential (Ek), resulting in hyperpolarization of the cell. [Cook, N. S., *Trends in Pharmacol. Sciences,* 9, pp. 21–28 (1988]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells under ischemic conditions.

The role of potassium channels in the operation of the smooth muscle of the human urinary bladder is discussed by S. Trivedi, et al. in *Biochemical and Biophysical Research Communications,* (1995), 213, No. 2, pp. 404–409.

A range of synthetic and naturally occurring compounds with BK opening activity have been reported. The *avena* pyrone extracted from *avena sativa*-common oats has been identified as a BK channel opener using a lipid bi-layer technique [International Patent application WO 93/08800, published May 13, 1993]. The flavanoid, Phloretin has been found to affect the opening of $Ca^{2+}$-activated potassium channels in myelinated nerve fibers of *Xenopus laevis* using outside-out patches [Koh, D-S., et al., *Neuroscience Lett.,* 165, pp. 167–170 (1994)].

Varia, S. A., et al., disclosed the use of phosphonomethoxy derivatives (i) as prodrugs of the hydantoin Phenytoin in *J. Pharm. Sci.* 73, pp. 1068–1073 (1984).

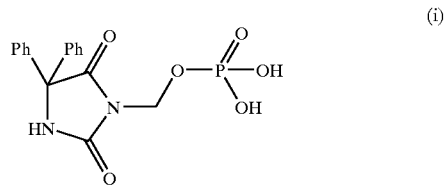

(i)

In International application WO 99/33846 published Jul. 8, 1999, Stella, V., et al., disclosed quaternary amine phosphates (ii) as prodrugs for amine containing drugs.

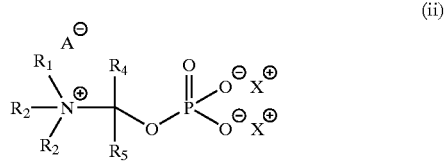

(ii)

Desai, R. C., et al., in U.S. Pat. No. 5,187,173 issued Feb. 16, 1993, teach that phosphonomethyl saccharine derivatives (iii) are useful as proteolytic enzyme inhibitors.

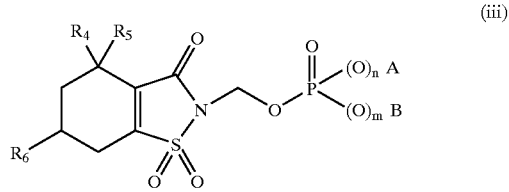

(iii)

In U.S. Pat. No. 5,939,405 issued Aug. 17, 1999, Starrett, et al. disclosed phosphate derivatives (iv) as useful prodrugs of diaryl 1,3,4-oxadiazolones which are modulators of the large-conductance, calcium-activated potassium (BK) channels.

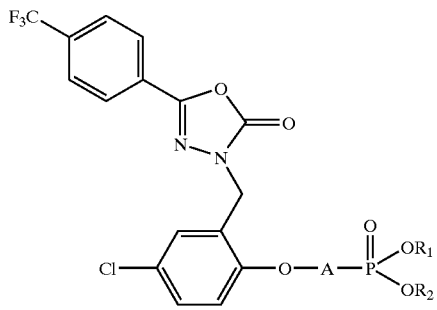

(iv)

Hewawasam, et al. demonstrated in U.S. Pat. No. 5,602,169 issued Feb. 11, 1997, that (3S)-(+)-(5-chloro-2-methoxyphenyl)-1,3-dihydro-3-fluoro-6-(trifluoromethyl)-2H-indol-2-one (compound of Formula (S)-II) is a modulator of large-conductance, calcium-activated potassium (BK) channels, and is useful for the treatment of ischemia.

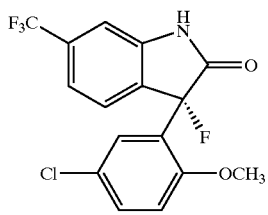

Compound of Formula (S)-II

The synthesis of the compound of Formula (S)-II and its utility to treat disorders sensitive to potassium channel opening, including cerebral ischemia and traumatic brain injury is described by Hewawasam, et. al. in U.S. Pat. No. 5,602,169. Due to the low aqueous solubility of the compound of Formula (S)-II, additives such as dimethylsulfoxide and propylene glycol, for example, must be employed in order to prepare solutions of the compound of Formula (S)-II suitable for intravenous injection (Gribkoff, et al., Nature Medicine, 2001, 7, 471–477).

SUMMARY OF THE INVENTION

The present invention provides novel phosphate derivatives of 3-fluorooxindoles having the general formula

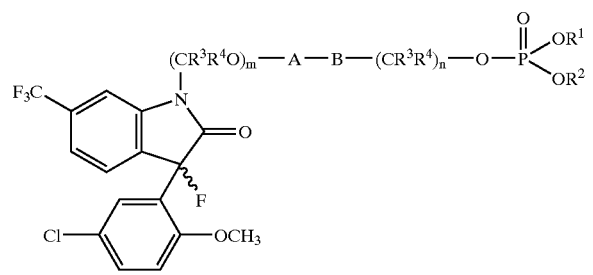

I wherein the wavy bond (∿) represents the racemate, the (R)-enantiomer or the (S)-enantiomer and A, B, $R^1$, $R^2$, $R^3$, $R^4$, m and n are as defined below, or a nontoxic pharmaceutically acceptable salt or solvate thereof. The phosphates of the present invention increase the water solubility of the 3-fluorooxindoles, and thereby decrease the amount of additives that need to be employed to deliver an intravenous dose of the oxindole. Upon systemic administration, the oxindole derivatives are transformed to liberate systemic levels of the fluorooxindole. The present invention also provides pharmaceutical compositions comprising said phosphate derivatives and to the method of treatment of disorders sensitive to potassium channel opening activity such as ischemia, stroke, convulsions, asthma, epilepsy, irritable bowel syndrome, migraine, traumatic brain injury, elevated intracranial pressure, spinal cord injury, sexual dysfunction, carbon monoxide poisoning and urinary incontinence.

DETAILED DESCRIPTION OF THE INVENTION

The present invention provides novel phosphate derivatives of the racemate, the (R)-enantiomer and (S)-enantiomer of 3-(5-chloro-2-methoxyphenyl)-1,3-dihydro-3-fluoro-6-(trifluoromethyl)-2H-indol-2-one (compound of Formula II) which is a potent opener of the large conductance, calcium-activated $K^+$-channels (BK channel) and the novel derivatives of the present invention have the general Formula I

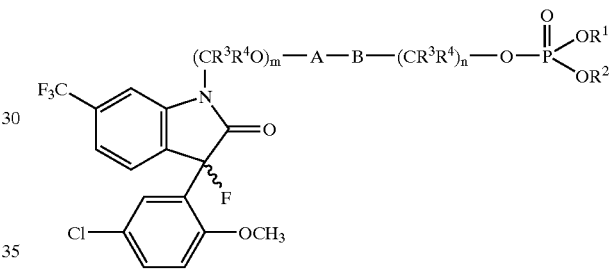

wherein the wavy bond (∿) represents the racemate, the (R)-enantiomer or the (S)-enantiomer;
A is a direct bond or (C=O);
B is a direct bond, oxygen or nitrogen;
m is 0 or 1;
n is 1, 2 or 3;
$R^1$ and $R^2$ each are independently hydrogen or a hydrolyzable ester group; and when $R^1$ is hydrogen, $R^2$ may also be —P(O)$OR^5OR^6$ or heteroaryl;
$R^3$ and $R^4$ each are independently hydrogen or $C_{1-4}$ alkyl; and
$R^5$ and $R^6$ each are independently hydrogen or a hydrolyzable ester group;
or a nontoxic pharmaceutically acceptable salt or solvate thereof.

The present invention also provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula I or a nontoxic pharmaceutically acceptable salt thereof. Preferably, the compounds of Formula I are useful in the treatment of ischemia, stroke, epilepsy, convulsions, asthma, irritable bowel syndrome, migraine, traumatic brain injury, elevated intracranial pressure, spinal cord injury, sexual dysfunction, carbon monoxide poisoning and urinary incontinence and other disorders sensitive to BK channel activating activity.

The terms "$C_{1-4}$ alkyl", and "$C_{1-6}$ alkyl" as used herein and in the claims (unless the context indicates otherwise) means straight or branched chain alkyl groups such as methyl, ethyl, propyl, isopropyl, butyl, pentyl, hexyl. Preferably, these groups contain from 1 to 2 carbon atoms. The term "heteroaryl" as used herein and in the claims is intended to include pyridinyl, thiophenyl, pyrimidinyl, thiazoyl, oxazoyl, isoxazoyl and the like.

Unless otherwise specified, the term "a hydrolyzable ester group" as used herein and in the claims is intended to include an ester group which is physiologically acceptable and hydrolyzable such as $C_{1-6}$ alkyl, benzyl, 4-methoxybenzyl, (lower)-alkanoyloxy(lower)alkyl, e.g., acetoxymethyl, propionyloxymethyl or pivaloyloxymethyl, (lower) alkoxycarbonyloxy(lower)alkyl, e.g., methoxycarbonyloxymethyl or ethoxycarbonyloxymethyl, (lower)-alkoxycarbonyl(lower)alkyl, e.g., methoxycarbonylmethyl or t-butoxycarbonylmethyl, 2-methoxy-carbonyloxyethyl, (5-methyl-2-oxo-1,3-dioxol-4-yl)methyl, dihydroxypropyl and the like.

The term "a nontoxic pharmaceutically acceptable salt" as used herein and in the claims is intended to include nontoxic base addition salts with inorganic and organic bases. The salt of compound I which may be represented herein by $M^{\oplus}$ includes the monoanionic, the dianionic and trianionic salts, for example, the mono sodium, the di sodium and the tri sodium salts. Suitable inorganic bases such as alkali and alkaline earth metal bases include metallic cations such as sodium, potassium, lithium, magnesium, calcium and the like. Suitable organic bases include amines such as ammonium, alkylamine, dialkylamine, trialkylamines, tetraalkylammonnium, pyridine, dibenzylamine, ethanolamine, N-methylglucamine, piperdine, N-methylpiperidine, N-methylmorpholine, proline, glycine, lysine, arginine, tris(hydroxymethyl)aminomethane, and other amines which have been used to form salts of carboxylic acids and phosphoric acids.

Generally, pharmaceutically acceptable salts of the invention are those in which the counter-ion does not contribute significantly to the toxicity or pharmacological activity of the salt. In some instances, they have physical properties which make them more desirable for pharmaceutical formulations, such as solubility, lack of hygroscopicity, compressibility with respect to tablet formation and compatibility with other ingredients with which the substance may be used for pharmaceutical purposes. The salts are routinely made by admixture of a Formula I compound wherein $R^1$ and $R^2$ are hydrogen with the selected base, preferably by contact in solution employing an excess of commonly used inert solvents such as water, ether, acetonitrile, dioxane, methylene chloride, isopropanol, methanol, ethanol, ethyl acetate and acetonitrile. They may also be made by metathesis or treatment with an ion exchange resin under conditions in which the appropriate ion of a salt of the substance of the Formula I compound is replaced by another ion under conditions which allow for separation of the desired species such as by precipitation from solution or extraction into a solvent, or elution from or retention on an ion exchange resin.

Certain compounds of the present invention including the pharmaceutically acceptable salts thereof can exist as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the composition that is sufficient to show a meaningful patient benefit, i.e., healing of acute conditions characterized by openers of large conductance calcium-activated $K^+$ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

In another aspect, this invention provides water-soluble prodrugs of the compound of the racemate, the (R)-enantiomer and the (S)-enantiomer of 3-(5-chloro-2-methoxyphenyl)-1,3-dihydro-3-fluoro-6-(trifluoromethyl)-2H-indol-2-one which is described in U.S. Pat. No. 5,602,169. As used herein the term prodrug denotes a derivative of an active drug which is converted after administration back to the active drug. More particularly, it refers to phosphate derivatives of 3-fluorooxindole drugs which are capable of undergoing hydrolysis of the ester moiety or oxidative cleavage of the ester so as to release active free drug. For example, the phosphate may be hydrolyzed by phosphatase enzymes in the host to produce a more active form of the desired 3-fluorooxindole. The physiologically hydrolyzable groups also serve as prodrugs by being hydrolyzed in the body to yield the parent drug per se, and thus, the water-soluble prodrugs of the present invention are preferred for administration of the parent drug.

In still another aspect, this invention provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula I or a nontoxic pharmaceutically acceptable salt, solvate or hydrate thereof. Preferably, the compounds of Formula I are useful in the treatment of ischemia, stroke, convulsions, epilepsy, asthma, irritable bowel syndrome, migraine, traumatic brain injury, elevated intracranial pressure, spinal cord injury, carbon monoxide poisoning, urinary incontinence and sexual dysfunction in both men (erectile dysfunction, for example, due to diabetes mellitus, spinal cord injury, radical prostatectomy, psychogenic etiology or any other cause) and women by improving blood flow to the genitalia, especially the corpus cavernosum, and other disorders sensitive to BK channel activating activity. Most preferably, the compounds of Formula I are useful in the treatment of cerebral ischemia/stroke.

In still yet another aspect, this invention provides pharmaceutical compositions comprising at least one compound of Formula I in combination with a pharmaceutical adjuvant, carrier or diluent.

The compounds of Formula I may be prepared by various procedures such as those illustrated herein in the examples, in the Reaction Schemes and variations thereof which would be evident to those skilled in the art. The various prodrug compounds of Formula I may advantageously be prepared from the active drug substance of Formula II which is itself prepared by the general procedure described in U.S. Pat. No. 5,602,169 and used as the starting material in the methods illustrated in Reaction Schemes 1 to 9.

The preparation of 3-fluorooxindoles of Formula Ia is illustrated in Reaction Scheme 1 wherein $M^{\oplus}$ is defined herein. It should be appreciated by those skilled in the art that, if desired, the use of two moles of base would produce the compound of Formula Ia as a dianionic salt. The compound of Formula II is treated with a chloromethyl phosphate and a base such as cesium carbonate in a solvent such as acetonitrile to produce the corresponding phosphate intermediate of Formula III. Removal of the protecting tertiary butyl groups is advantageously effected by treating with an acid such as trifluoroacetic acid and treating the resulting phosphate with base affords the compound of Formula Ia.

REACTION SCHEME 1

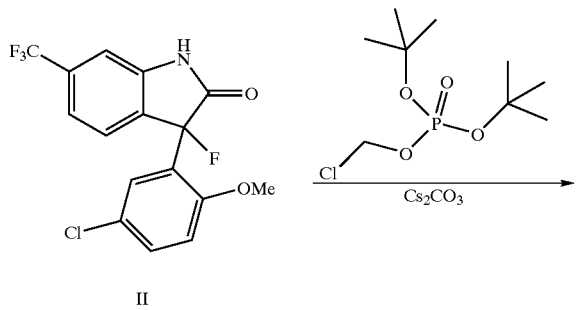

REACTION SCHEME 2

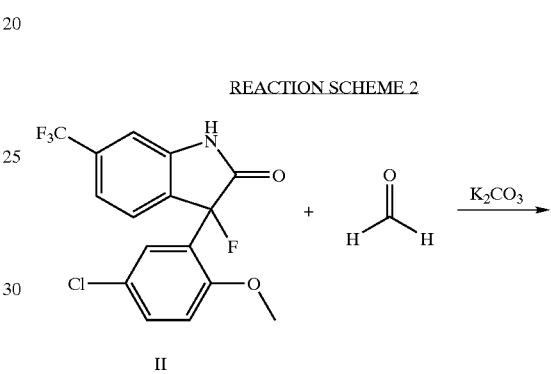

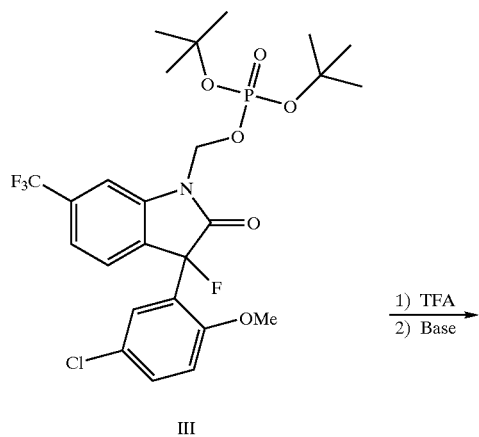

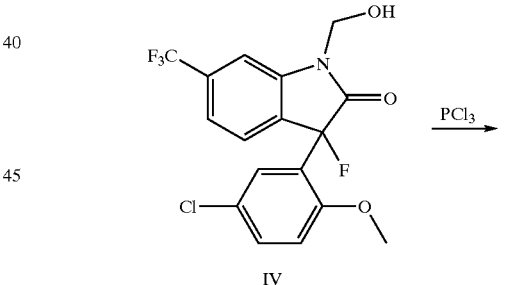

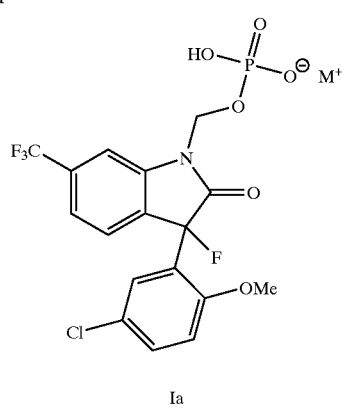

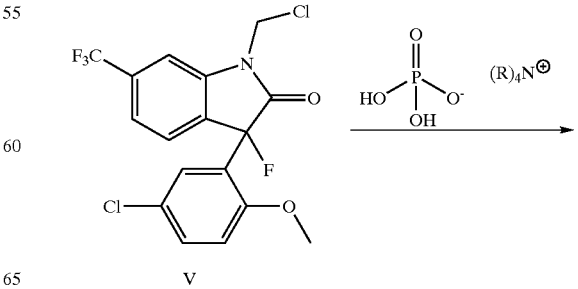

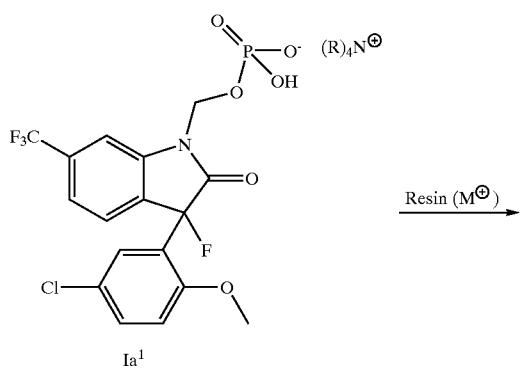
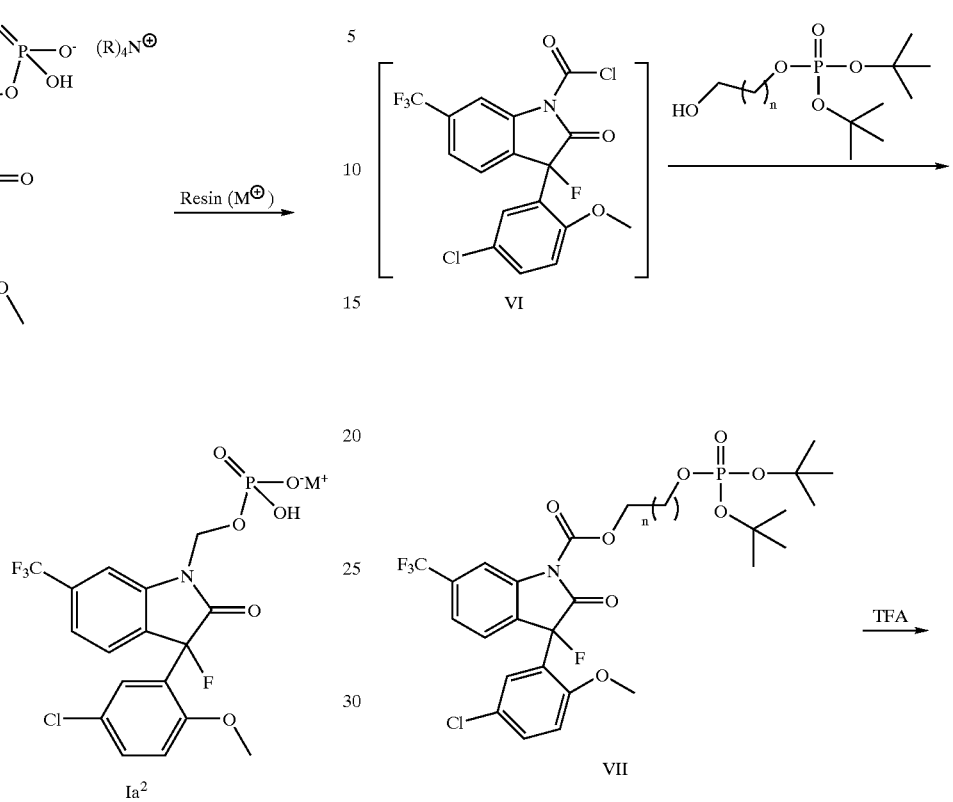

An alternative synthesis of the compounds of Formula Ia in which the counterion can be varied in a facile manner is depicted in Reaction Scheme 2, wherein R is $C_{1-4}$ alkyl and $M^\oplus$ are as defined herein. Acylation of the compound of Formula II with an acylating agent such as formaldehyde affords the hydroxymethyl adduct of Formula IV. Displacement of the hydroxyl group with a halogenating agent such as phosphorous trichloride provides the chloromethyl lactam of Formula V. Phosphorylation with an ammonium phosphate gives the ammonium phosphate of Formula Ia$^1$. Using an ion exchange resin which has been preloaded with the desired counterion, provides the compound of Formula Ia$^2$, wherein $M^\oplus$ is preferably a sodium or potassium cation.

REACTION SCHEME 3

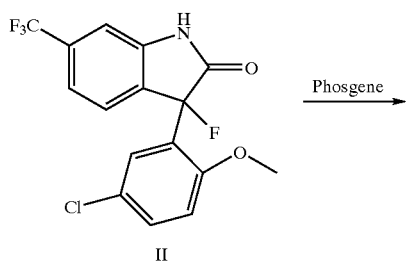

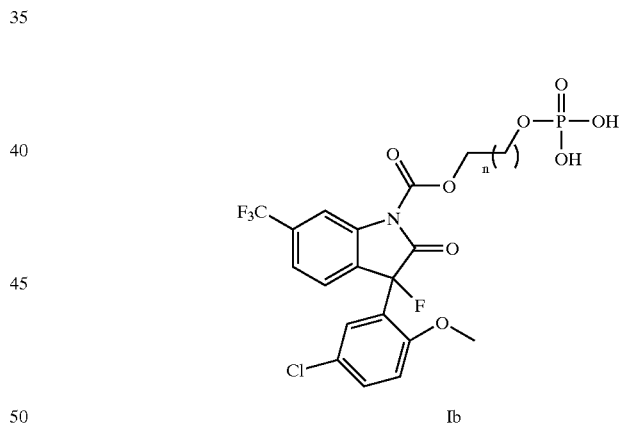

When it is desired to prepare the compounds of Formula Ib, as illustrated in Reaction Scheme 3, the compound of Formula II is acylated with an agent such as phosgene to provide a chloroformate of Formula VI. Displacement of the chlorine leaving group with a hydroxyalkyl phosphate results in the compounds of Formula VII, wherein n is as defined herein. Removal of the tertiary butyl groups with an acid such a trifluoroacetic acid yields the compounds of Formula Ib.

REACTION SCHEME 4

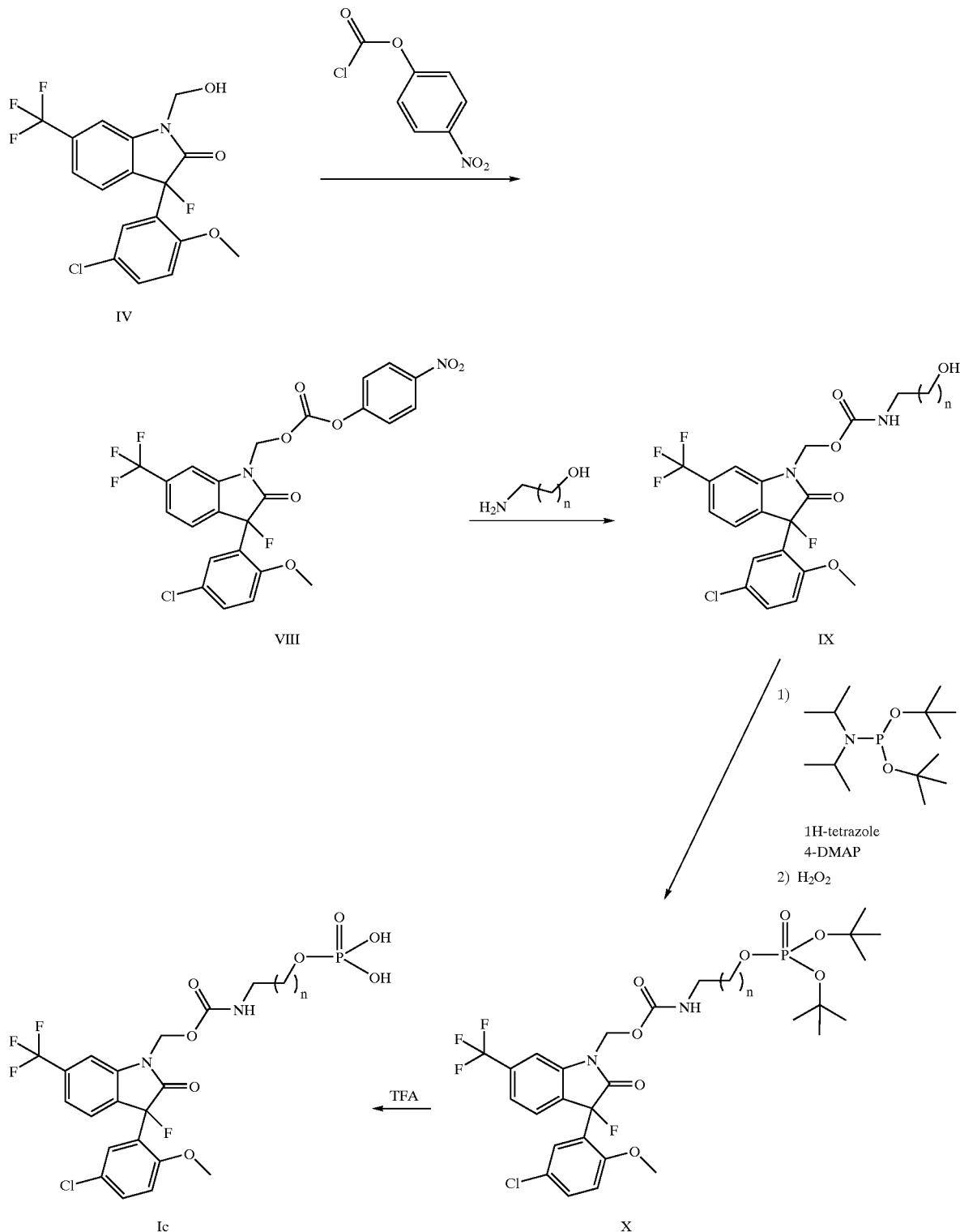

The preparation of compounds of Formula Ic is depicted in Reaction Scheme 4, wherein n is as defined herein. Acylation of the compound of Formula IV with a chloroformate provides a carbonate of Formula VIII. Displacement of the nitrophenol leaving group with an aminoalkyl alcohol gives carbamates of the Formula IX, which can be phosphorylated with a phosphoramidate, followed by oxidation of the phosphorous, to provide phosphates of Formula X. Removal of the tertiary butyl groups with an acid such as trifluoroacetic acid yields compounds of Formula Ic.

REACTION SCHEME 5

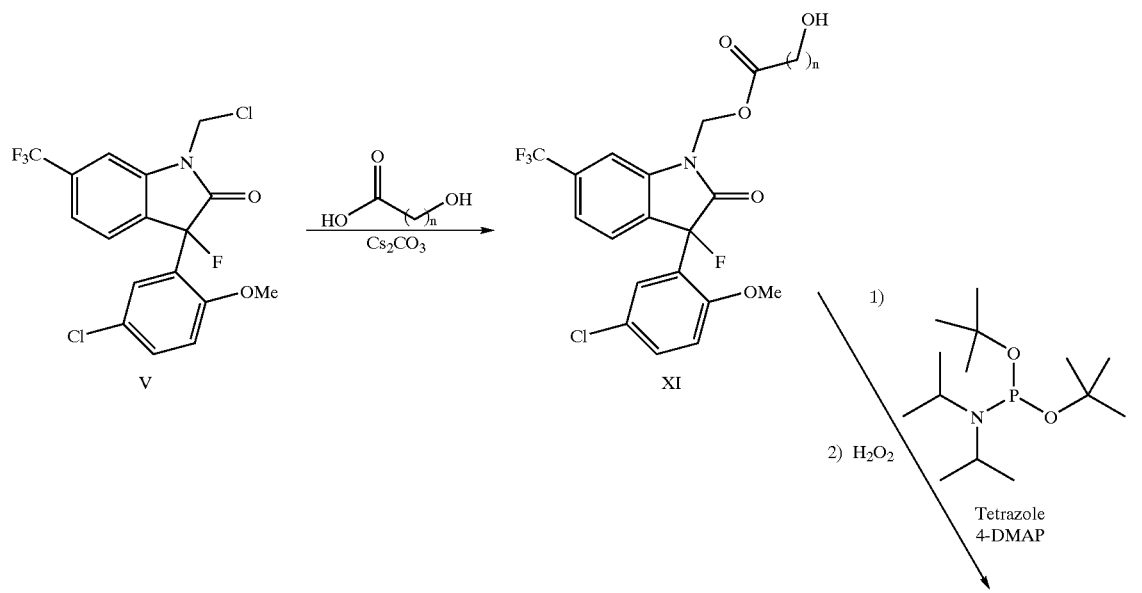

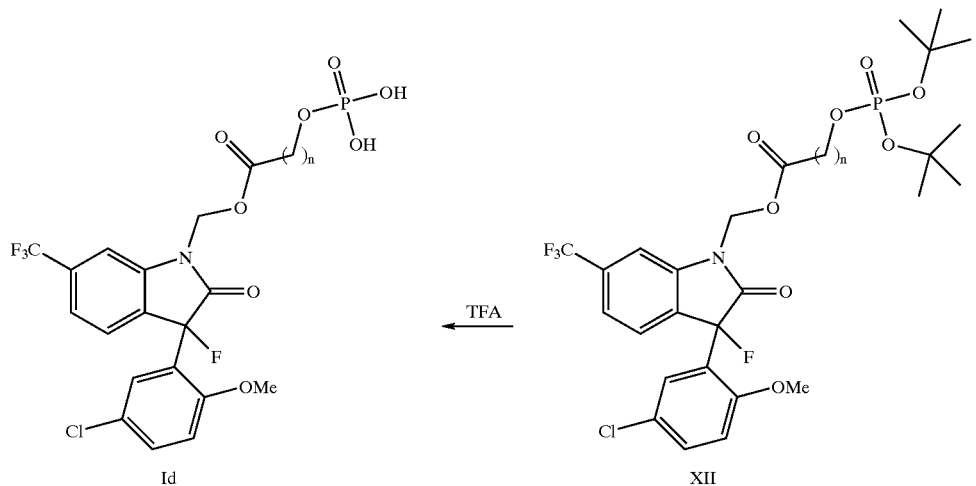

Esters of Formula Id can be performed as shown in Reaction Scheme 5, wherein n is as defined herein. Displacement of the chloro leaving group in compounds of Formula V with hydroxy alkyl acids provides esters of Formula XI, which can be phosphorylated with a phosphoramidate, followed by oxidation of the phosphorous to afford phosphates of Formula XII. Phosphates of the Formula Id can be obtained by deprotection of the compounds of Formula XII with an acid such as trifluoroacetic acid.

REACTION SCHEME 6

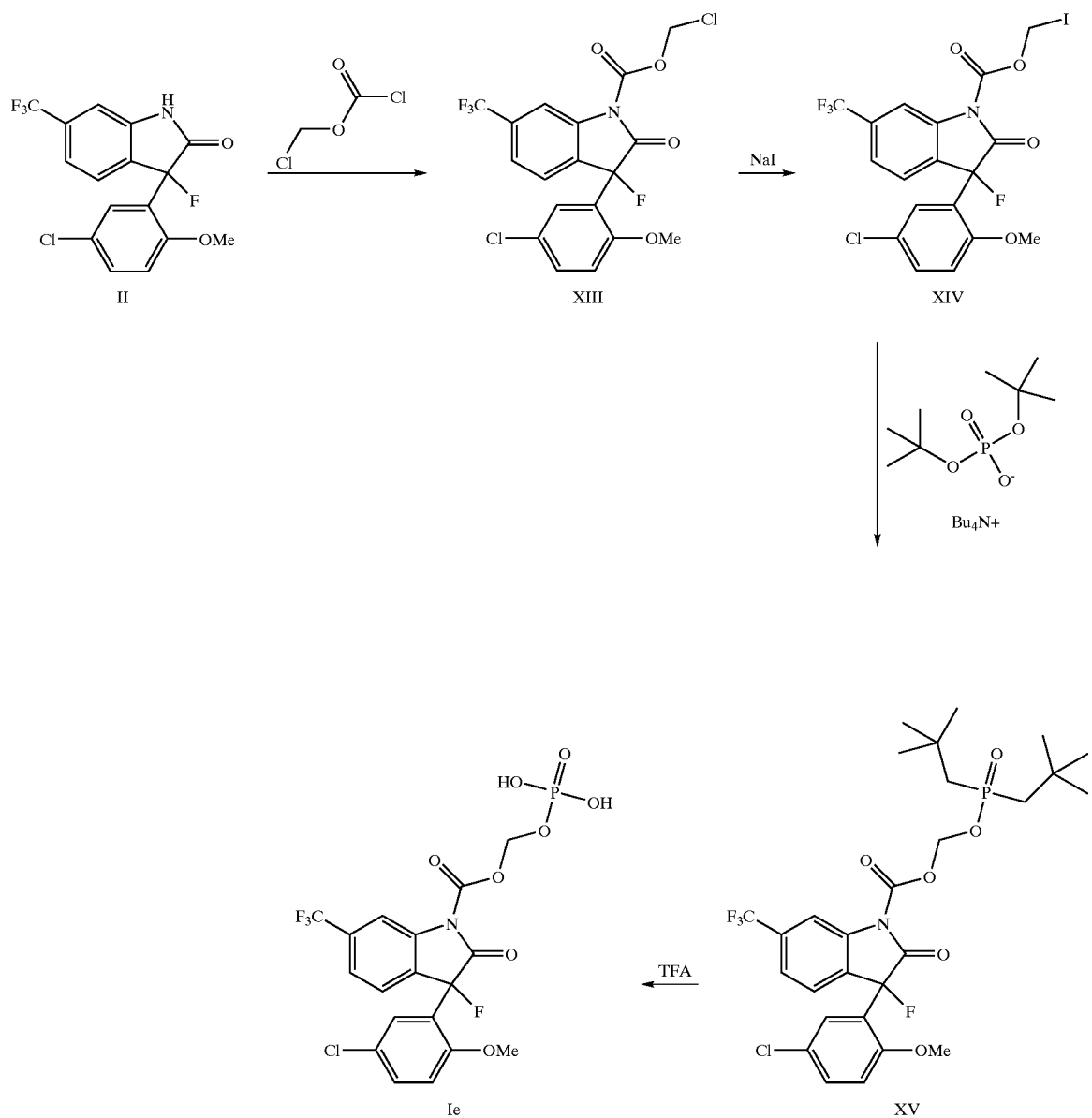

The preparation of carbamates of Formula Ie is illustrated in Reaction Scheme 6. Acylation of compounds of Formula II with an acylating agent such as chloromethyl chloroformate provides halomethyl carbamates of Formula XIII. Displacement of the chloride by sodium iodide gives iodomethyl carbamates of Formula XIV. Displacement of the iodide with a phosphates gives protected phosphates of Formula XV, which can be deprotected with an acid such as trifluoroacetic acid to afford carbamates of Formula Ie.

REACTION SCHEME 7

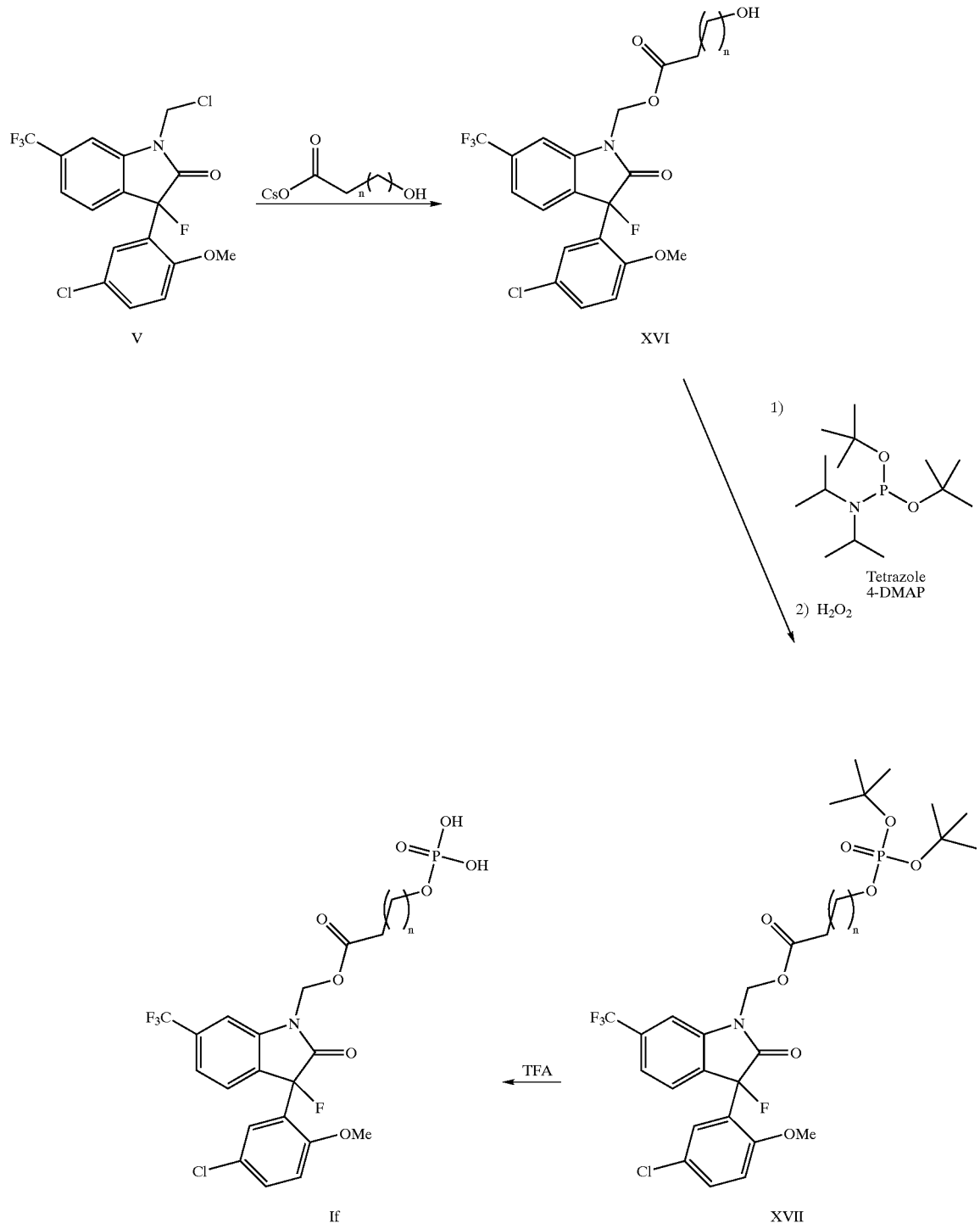

Phosphonoalkyl esters of the Formula If can be prepared as illustrated in Reaction Scheme 7, wherein n is a defined herein. Displacement of the chloro leaving group of the compound of Formula V with a hydroxy alkyl acid provides hydroxy alkyl esters of Formula XVI. Phosphorylation of the alcohol with a phosphoramidate, followed by oxidation of the phosphorous affords compounds of Formula XVII, which can be deprotected with an acid such as trifluoroacetic acid to yield phosphates of Formula If.

REACTION SCHEME 8

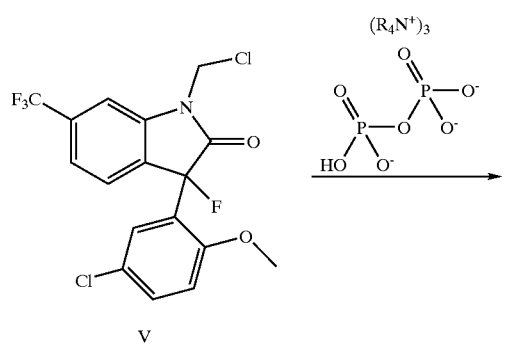

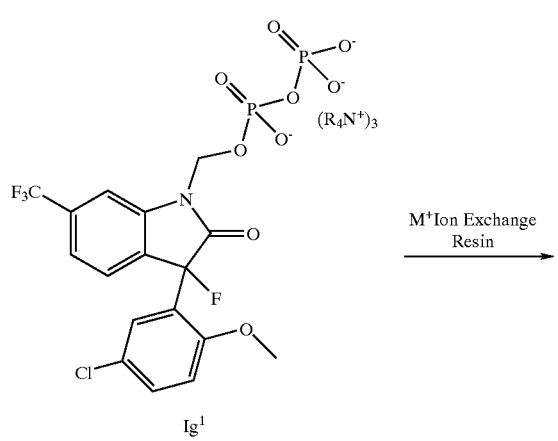

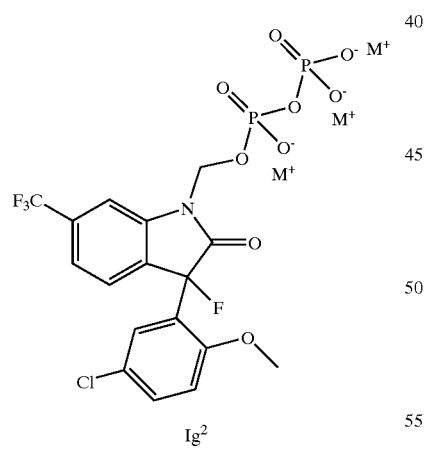

Reaction Scheme 8 depicts preparation of pyrophosphates of Formula Ig, wherein R and M$^\oplus$ are as defined herein. Displacement of the chloro leaving group of compounds of Formula V with an ammonium pyrophosphate afforded ammonium pyrophosphates of Formula Ig$^1$, which could be treated with an ion exchange resin to provide pyrophosphates of Formula Ig$^2$.

REACTION SCHEME 9

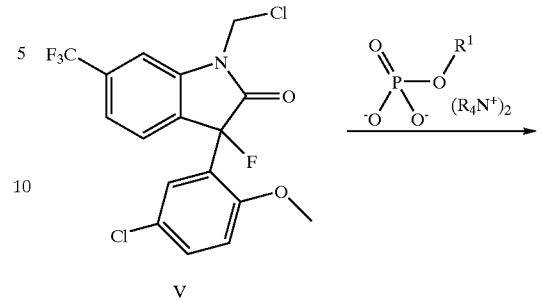

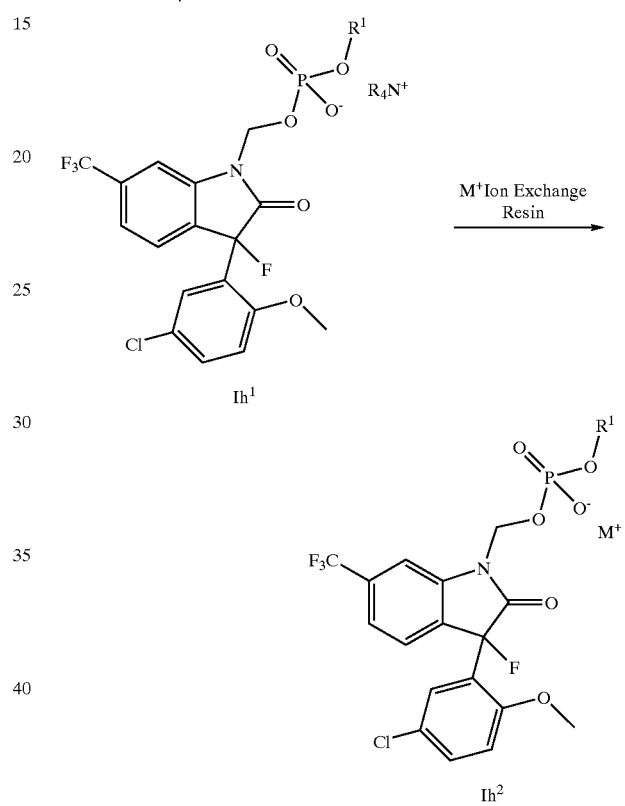

Displacement of the chloro group of compounds of Formula V with phosphates provides ammonium alkyl phosphates of Formula Ih$^1$, as depicted in Reaction Scheme 9, wherein R, R$^1$, and M$^+$ are as defined herein. Treatment of the ammonium phosphates with ion exchange resin affords the alkyl phosphates of Formula Ih$^2$.

In a preferred embodiment of the invention, the compounds have the Formula I'

I'

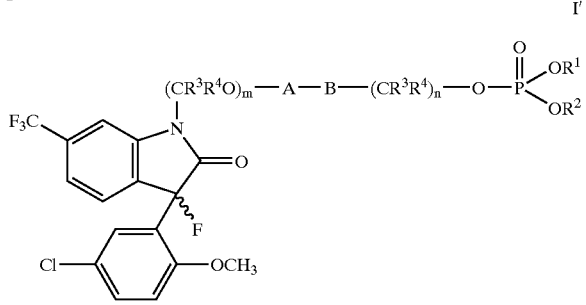

wherein the wavy bond (∿) represents the racemate, the (R)-enantiomer or the (S)-enantiomer;
A is a direct bond or (C=O);
B is a direct bond or oxygen;
m is 0 or 1;
n is 1, 2 or 3;
$R^1$ and $R^2$ each are independently hydrogen or a hydrolyzable ester group; and when $R^1$ is hydrogen, $R^2$ may also be —P(O)OR$^5$OR$^6$;
$R^3$ and $R^4$ each are independently hydrogen or $C_{1-4}$ alkyl; and
$R^5$ and $R^6$ each are independently hydrogen or a hydrolyzable ester group;
or a nontoxic pharmaceutically acceptable salt or solvate thereof.

In a more preferred embodiment of the invention, the wavy bond (∿) represents the (S)-enantiomer in the compounds of Formula I'.

In another preferred embodiment of the invention, the compounds of Formula I are selected from the group comprising of:
(S)-phosphoric acid mono-[3-(5-chloro-2-methoxy-phenyl)-3-fluoro-2-oxo-6-trifluoromethyl-2,3-dihydro-indol-1-ylmethyl] ester;
(R)-phosphoric acid mono-[3-(5-chloro-2-methoxy-phenyl)-3-fluoro-2-oxo-6-trifluoromethyl-2,3-dihydro-indol-1-ylmethyl] ester;
(S)-3-(5-chloro-2-methoxy-phenyl)-3-fluoro-2-oxo-6-trifluoromethyl-2,3-dihydro-indole-1-carboxylic acid 2-phosphonooxy-propyl ester;
(S)-3-(5-chloro-2-methoxy-phenyl)-3-fluoro-2-oxo-6-trifluoromethyl-2,3-dihydro-indole-1-carboxylic acid 2-phosphonooxy-ethyl ester;
(S)-(2-phosphonooxy-ethyl)-carbamic acid 3-(5-chloro-2-methoxy-phenyl)-3-fluoro-2-oxo-6-trifluoromethyl-2,3-dihydro-indol-1-ylmethyl ester;
(S)-phosphonooxy-acetic acid 3-(5-chloro-2-methoxy-phenyl)-3-fluoro-2-oxo-6-trifluoromethyl-2,3-dihydro-indol-1-ylmethyl ester;
(S)-3-(5-chloro-2-methoxy-phenyl)-3-fluoro-2-oxo-6-trifluoromethyl-2,3-dihydro-indole-1-carboxylic acid phosphonooxymethyl ester;
(S)-3-phosphonooxy-propionic acid 3-(5-chloro-2-methoxy-phenyl)-3-fluoro-2-oxo-6-trifluoromethyl-2,3-dihydro-indol-1-ylmethyl ester;
(S)-pyrophosphoric acid [3-(5-chloro-2-methoxy-phenyl)-3-fluoro-2-oxo-6-trifluoro methyl-2,3-dihydro-indol-1-yl methyl ester;
(S)-phosphoric acid-[3-(5-chloro-2-methoxy-phenyl)-3-fluoro-2-oxo-6-trifluoromethyl-2,3-dihydro-indol-1-ylmethyl ester] methyl ester; and
(S)-phosphoric acid-[3-(5-chloro-2-methoxy-phenyl)-3-fluoro-2-oxo-6-trifluoromethyl-2,3-dihydro-indol-1-ylmethyl ester] ethyl ester;
or a nontoxic pharmaceutically acceptable salt or solvate thereof.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula I or a nontoxic pharmaceutically acceptable salt, solvate or hydrate thereof.

In yet another embodiment, this invention relates to a method for treating ischemia, convulsions, epilepsy, asthma, irritable bowel syndrome, migraine, traumatic brain injury, elevated intracranial pressure, spinal cord injury, carbon monoxide poisoning, male and female sexual dysfunction, urinary incontinence and especially stroke in a mammal in need thereof, which comprises administering to said mammal a therapeutically effective amount of a compound of Formula I or a nontoxic pharmaceutically acceptable salt, solvate or hydrate thereof.

Biological Activity

Potassium ($K^+$) channels are structurally and functionally diverse families of $K^+$-selective channel proteins which are ubiquitous in cells, indicating their central importance in regulating a number of key cell functions [Rudy, B., Neuroscience, 25, pp. 729–749 (1988)]. While widely distributed as a class, $K^+$ channels are differentially distributed as individual members of this class or as families. [Gehlert, D. R., et al., Neuroscience, 52, pp. 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of $K^+$ channels, the large-conductance $Ca^{2+}$-activated $K^+$ channels (BK or BK channels), is regulated by transmembrane voltage, intracellular $Ca^{2+}$, and a variety of other factors such as the phosphorylation state of the channel protein. [Latorre, R., et al., Ann. Rev. Physiol., 51, pp. 385–399 (1989)]. The large, single channel-conductance (generally >150 pS) and high degree of specificity for $K^+$ of BK channels indicates that small numbers of channels could profoundly affect membrane conductance and cell excitability. Additionally, the increase in open probability with increasing intracellular $Ca^{2+}$ indicates involvement of BK channels in the modulation of $Ca^{2+}$-dependent phenomena such as secretion and muscular contraction. [Asano, M., et al., J. Pharmacol. Exp. Ther., 267, pp. 1277–1285 (1993)].

Openers of BK channels exert their cellular effects by increasing the open probability of these channels [McKay, M. C., et al., J. Neurophysiol., 71, pp. 1873–1882 (1994); and Olesen, S.-P., Exp. Opin. Invest. Drugs, 3, pp. 1181–1188 (1994)]. This increase in the opening of individual BK channels collectively results in the hyperpolarization of cell membranes, particularly in depolarized cells, produced by significant increases in whole-cell BK-mediated conductance.

The ability of the compound of Formula II to open BK channels and increase whole-cell outward ($K^+$) BK-mediated currents was assessed under voltage-clamp conditions by determining their ability to increase cloned mammalian (mSlo or hSlo) BK-mediated outward current heterologously expressed in Xenopus oocytes [Butler, A., et al., Science, 261, pp. 221–224 (1993); and Dworetzky, S. I., et al., Mol. Brain Res., 27, pp. 189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., *J. Biol. Chem*, 265, pp. 11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compound profiled did not effect non-BK native currents in the oocytes. The compound of Formula II was shown in at least 5 oocytes at a concentration of 10 $\mu$M to increase BK current to 170% of control of IBTX-sensitive current. Recordings were accomplished using standard two-electrode voltage clamp techniques [Stuhmer, W., et al., *Methods in Enzymology*, 207, pp. 319–339 (1992)]; voltage-clamp protocols consisted of 500–750 ms duration step depolarizations from a holding potential of −60 mV to +140 mV in 20 mV steps. The experimental media (modified Barth's solution) consisted of (in mM): NaCl (88), NaHCO$_3$ (2.4), KCl (1.0), HEPES (10), MgSO$_4$ (0.82), Ca(NO$_3$)$_2$ (0.33), CaCl$_2$ (0.41); pH 7.5.

The compound of Formula (S)-II or a prodrug of Formula I was administered intravenous bolus to male Sprague-Dawley rats (n=3 rats/timepoint) at a target dose equivalent to 1 mg/kg of the compound of Formula (S)-II. At T=0.25, 1 and 2 hours post-dose, whole blood samples were collected and extracted with acetonitrile. Blood extracts were analyzed by LC/MS/MS for levels of the compound of Formula (S)-II. Table 1 shows a comparison of estimates of truncated 0.25–2 hours AUC of the compound of Formula (S)-II after administering either the compound of Formula II or the prodrug of Formula I. For example, as shown in Table 1 following the administration of prodrugs of Formula I, the compound of Formula (S)-II was detected in the blood of this rat model.

TABLE 1

Rat Blood Levels of Compound (S)-II after Prodrug Administration

| Example | Truncated Blood AUC$_{(0.25-2\ hr)}$ (ng*hr/mL) Compound of Formula (S)-II |
|---|---|
| Compound of Formula (S)-II | 261 |
| 5 | 106 |
| 2 | 188 |
| 10 | 135 |

To determine the ability of the compounds of the present invention to reduce cell loss resulting from neuronal ischemia, a standard focal cerebral ischemia is induced by permanent occlusion of the left middle cerebral artery (MCA) and common carotid artery (CCA) with one hour occlusion of the right CCA in the Wistar rat. The surgeries are performed using the sub-temporal approach of A. Tamura, et al., *J. Cereb. Blood Flow Metab.*, 1, pp. 53–60, (1981) and its modifications [K. Osborne, et al., *J. Neurol Neurosurg. Psychiatry*, 50, pp. 402–410 (1987) and S. Menzies, et al., *Neurosurgery*, 31, pp. 100–107, (1992)].

The compound of Formula II was evaluated in the focal stroke model involving permanent occlusion of the left MCA (MCAO) and CCA (CCAO) and temporary occlusion of the right CCA in the Wistar rat [Gribkoff, et al. *Nature Med.* 7, pp. 471–477 (2001)]. This procedure results in a reliably large neocortical infarct volume that is measured by means of vital dye exclusion in serial slices through the brain 24 hours after MCAO. In the present test, compounds were administered using an i.v. or i.p. route of administration two hours after occlusion. For example, in this model the compound of Formula II significantly reduced the cortical infarct volume by about 28% when administered intravenously (0.3 mg//kg) as a single bolus two hours after middle cerebral artery occlusion as compared to vehicle-treated control.

To determine the ability of the compounds of the present invention to decrease the amount of neuronal damage following head injury, a standard model of traumatic brain injury was employed. The rat traumatic brain injury (TBI) model is used to evaluate compounds for effectiveness in reversing or preventing the deleterious effects of a concussion-like injury. In general, rats in this model were anesthetized, a craniotomy is performed (surgical opening of the skull), and then saline was injected into the opening to produce a precise pulse of increased intracranial pressure (commonly called a fluid percussion injury). Animals were administered compound at the specified doses at 15 minutes following trauma. Animals were euthanized 48 hours post TBI.

Moderate diffuse brain injury (defined by McIntosh, et al. *Neuroscience*, 28:233–44 (1989)) was induced by a fluid-percussion device. The apparatus produces contusion via the rapid injection of a saline pulse [~2.1 to 2.7 atmospheres of pressure (atm)] at a constant duration (21–23 millisecond) into a closed cranial cavity. The saline pulse results in the brief displacement and deformation of the underlying cortex. This model is thought to mimic the clinical situation where a patient experiences a concussion-like injury characterized by brief neurological and systemic physiological alterations without severe structural damage. The fluid percussion device produces brain injury without directly impacting the brain. Diffuse brain injury is achieved by the release of a weighted (4.8 kg) metal pendulum from a predetermined height (McIntosh, et al 1989) that strikes a cork-covered piston at the end of a Plexiglass cylindrical reservoir filled with isotonic saline. Varying volumes of saline are injected into the closed cranial cavity producing a pulse of increased intracranial pressure (ICP). Varying the height of the pendulum controls the magnitude of the injury.

In this experiment the pressure pulses were measured extracranially by a transducer located in the injury device. Following the induction of anesthesia, the trauma screw was tightly connected to the fluid percussion device, and an injury of moderate severity [~2.1 to 2.7 atm], was induced based on a scale established by McIntosh, et al 1989. The pulses were recorded on a storage oscilloscope triggered photoelectrically by descent of the pendulum. Following fluid percussion, the cap created by the trauma screw, the stainless steel screw, and the cranioplastic cement were all removed and the wound closed by non-absorbable suture (3–0). Animals remaining apneic for more than 60 seconds post-injury were immediately euthanatized. Rats were maintained on a water recirculating heating pad until respiration normalized and they were ambulatory. Animals were euthanized and brains removed for assessment of edema at 48 hours by measurement of water content as described previously (McIntosh, et al 1989).

The compound of Formula (S)-II has previously been shown to produce significant reductions in edema in several regions adjacent to the impact zone [Cheney, et al. *J. Cer. Blood Flow & Metab.* 21:396–403(2001)]. The compound of Formula Ia of the present invention, produced significant reductions in edema in adjacent cortex that were comparable to those produced by the compound of Formula (S)-II when both were delivered at equivalent molar doses in the same animal model of traumatic brain injury.

In an alternate method, the severity of brain damage was assessed by Intracranial Pressure (ICP) measurement at various intervals post fluid percussion up to 24 hours. In brief, prior to the fluid percussion a burr hole was made 1 mm from the sagittal suture, centered over the right parietal cortex 5 mm from lambda, 5 mm from bregma. Following fluid percussion injury, the trauma cap and cranioplastic cement were removed. In order to achieve adequate ICP values, while still under anesthesia, the craniotomy cap was re-inserted in its original location post fluid percussion. Pre-cut sterile foil was also placed over the craniotomy cap. Cranioplastic cement was placed over the foil to seal the brain cavity. To obtain continuous ICP measurements the probe was inserted into the burr hole and fixed by cranioplastic cement, the animal was then sutured (using 3–0) and the rat was placed in a Hopper cage to allow for free movement during the experiment. Next, the ICP transducer was connected to a Codman ICP monitor for continuous ICP measurements up to 24 hrs post-TBI or post-sham injury. During this time the animal had regular access to water and food. At 24 hrs post-TBI the experiment was terminated and animals were euthanatized by sodium pentobarbital overdose (130 mg/kg; i.p.).

These experiments consist of a sham-vehicle group (SV), a TBI-vehicle group (TV), sham-drug treated groups (SD; 0.08 mg/kg compound of Example 14 [dose equivalent of 0.05 mg/kg compound of Formula (S)-II]) and TBI-drug treated groups (TD; 0.08 mg/kg compound of Example 14). Each sham group acted as a control for the corresponding TBI group. All of the animals underwent anesthesia and surgery. In the TBI groups, brain injury was induced using the lateral fluid-percussion model. Drug treatment was initiated at 15 minutes post-TBI or sham-injury. A compound was considered to be effective if it significantly reduced ICP compared to its corresponding sham injured group at any given time point (significant by ANOVA compared to corresponding sham group; significant by t-test). Five minutes post injury absolute ICP (raw data) increased 6.8 mmHg units in TV animals compared to SV animals (SV-5.55 vs. TV-12.35). During the next 30 minutes post TBI ICP values decreased and finally stabilized at 8.55 mmHg (TV) and 5 mmHg (SV), respectively. TD was significantly different from TV at 45 minutes, 60 minutes, 2 hours, 3 hours, 4 hours, and 24 hours post-TBI with the most significant reduction (3.1 mmHg units) at 60 minutes post injury (or 45 minutes post-drug injection (TV-8.15 vs TD-5.05 mmHg). Assessing intra-animal mean ICP reduction, TD was significantly reduced compared to TV at 30 minutes (−2.85 vs. −1.15 mmHg), 45 minutes (−3.95 vs. −1.35), 60 min (−4.5 vs. −1.55), 2 hours (−4.3 vs. −1.95), 3 hr (−4.3 vs. 1.8), 4 hours (−4.15 vs. −1.3), and 24 hours (−3.05 vs. −0.9) post injury with the maximal reduction observed at 60 min post injury (or 45 minutes post-drug administration. SD values did not significantly differ from SV until 4 hours post-sham injury (−1.5 [SV] vs. −2.1 [SD] mmHg), however at 24 hours-post drug administration the ICP reduction observed between the groups had abated.

The results of the above tests demonstrate that the novel oxindole compounds of the present invention are useful for the treatment of human disorders arising from dysfunction of cellular membrane polarization and conductance and, preferably, are indicated for the treatment of ischemia, stroke, convulsions, epilepsy, asthma, irritable bowel syndrome, migraine, traumatic brain injury, elevated intracranial pressure, spinal cord injury, carbon monoxide poisoning, sexual dysfunction, and urinary incontinence and other disorders sensitive to BK channel activating activity.

Most preferably, the compounds of Formula I are useful in the treatment of cerebral ischemia/stroke, traumatic brain injury and elevated intracranial pressure.

The compounds of Formula I or pharmaceutical compositions thereof are useful in the treatment, alleviation or elimination of disorders or other disorders associated with the BK channels. Such disorders include ischemia, stroke, convulsions, epilepsy, asthma, irritable bowel syndrome, migraine, traumatic brain injury, elevated intracranial pressure, spinal cord injury, carbon monoxide poisoning, sexual dysfunction and urinary incontinence and other disorders sensitive to potassium channel openers.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 ng/kg to 10 mg/kg body weight. For parenteral administration, the dose may be in the range of 0.1 ng/kg to 10 mg/kg body weight for intravenous administration. The active ingredient will preferably be administered either with a bolus injection or bolus injection followed by continuous infusion; continuously; or in equal doses from one to four times a day.

However, it will be understood that the amount of the compound actually administered will be determined by a physician, in the light of the relevant circumstances, including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the meaning of the invention.

Description of Specific Embodiments

In the following examples, all temperatures are given in degrees Centigrade. Melting points were recorded on a Gallenkamp capillary melting point apparatus temperatures are uncorrected. Proton magnetic resonance ($^1$H NMR) was recorded on a Bruker AC 300. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular (MH$^+$) or (M–H)$^-$ was determined on a Finnigen TSQ 7000. High resolution mass spectra was determined on a Kratos MS50 in FAB mode using cesium iodide/glycerol as internal reference. The element analysis are reported as percent by weight.

The following preparations illustrate procedures for the preparation of intermediates and methods for the preparation of products according to this invention. It should also be evident to those skilled in the art that appropriate substitution of both the materials and methods disclosed herein will produce the examples illustrated below and those encompassed by the scope of this invention.

EXAMPLE 1

(S)-Phosphoric acid mono-[3-(5-chloro-2-methoxy-phenyl)-3-fluoro-2-oxo-6-trifluoromethyl-2,3-dihydro-indol-1-ylmethyl] ester, bis-t-butyl ammonium salt; (S)-Ia:

Step A. Phosphoric acid di-tert-butyl ester 3-(5-chloro-2-methoxy-phenyl)-3-fluoro-2-oxo-6-trifluoromethyl-2,3-dihydro-indol-1-ylmethyl ester ((S)-III)

To a 250 mL flask containing (3S)-3-(5-chloro-2-methoxy-phenyl)-3-fluoro-6-trifluoromethyl-1,3-dihydro-indol-2-one ((S)-II) (prepared according to U.S. Pat. No. 5,808,095) (2.00 g, 5.57 mmol) was added 20 mL anhydrous acetonitrile, cesium carbonate (2.35 g, 7.24 mmol) and chloromethyl-di-t-butylphosphate (2.16 g, 8.36 mmol). The reaction was stirred for 24 hours at room temperature, then the solvent was evaporated in vacuo. The resulting crude residue was purified by flash chromatography (silica gel; 4:1 Hexanes:EtOAc) affording the title compound (2.12 g, 65%) as a white solid. $^1$H NMR (CDCl$_3$ 400 MHz): δ=7.78 (s, 1H), 7.47 (s, 1H), 7.34–7.31 (m, 2H), 7.25 (d, 1H, J=7 Hz), 6.74 (d, 1H, J=7 Hz), 5.71 (dd, 1H, J=12.0, 6.8 Hz), 5.59 (dd, 1H, J=12.0, 6.8 Hz), 3.53 (s, 3H), 1.52 (s, 9H), 1.51 (s, 9H).

Step B. (S)-Phosphoric acid mono-[3-(5-chloro-2-methoxy-phenyl)-3-fluoro-2-oxo-6-trifluoromethyl-2,3-dihydro-indol-1-ylmethyl] ester, bis-t-butyl ammonium salt; (S)-Ia To a 100 mL flask containing phosphoric acid di-tert-butyl ester 3-(5-chloro-2-methoxy-phenyl)-3-fluoro-2-oxo-6-trifluoromethyl-2,3-dihydro-indol-1-ylmethyl ester ((S)-III) (0.500 g, 0.860 mmol) was added 10 mL anhydrous dichloromethane, and trifluoroacetic acid (0.196 g, 1.72 mmol). The reaction was allowed to stir at room temperature for 24 hours. The dichloromethane was evaporated in vacuo, and the crude foam was purified by reverse phase chromatography (C$_{18}$ 2:1CH$_3$CN:H$_2$O), then the isolated free phosphate was dissolved in ethyl acetate and t-butyl amine (0.251 g, 3.44 mmol) was added and the solvent was evaporated in vacuo producing the title compound (0.100 g, 19%) as a white powder. $^1$H NMR (D$_2$O 500 MHz): δ=7.89 (s, 1H), 7.78 (s, 1H), 7.50 (m, 2H), 7.41 (d, 1H, J=6.4 Hz), 7.03 (d, 1H, J=6.4 Hz), 5.63 (dd, 1H, J=12.0, 6.8 Hz), 5.56 (dd, 1H, J=12.0, 6.8 Hz), 3.56 (s, 3H), 1.36 (s, 18H); $^{31}$P NMR (D$_2$O 202 MHz) δ=1.68; LRMS [M–H]$^-$467.9.

EXAMPLE 2

(S)-Phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt; (S)-Ia[1]

Step A. (S)-3-(5-Chloro-2-methoxy-phenyl)-3-fluoro-1-hydroxymethyl-6-trifluoromethyl-1,3-dihydro-indol-2-one ((S)-IV)

To a mixture of (S)-3-(5-chloro-2-methoxy-phenyl)-3-fluoro-6-trifluoromethyl-1,3-dihydro-indol-2-one ((S)-II) (60.0 g, 0.167 mol) and K$_2$CO$_3$ (27.7 g, 0.20 mol) in THF (600 mL) was added formaldehyde (37% solution in H$_2$O, 240 mL, 3.2 mol) followed by H$_2$O (300 mL). The lightly turbid mixture was stirred at room temperature for 3 hours, and diluted with diethyl ether (1000 mL). The organic layer was separated. The aqueous layer was washed with ether (200 mL×2). The combined organic layer was washed with brine, dried over Na$_2$SO$_4$. Evaporation of solvents provided the title compound as a white dry foam (64.5 g, 99% yield). LC/MS m/e: 390 (MH$^+$), 96% purity. $^1$H NMR (CDCl$_3$): δ 3.50 (s, 3H), 5.28 (m, 1H), 5.45 (m, 1H), 6.75 (dd, J=1.5, 6.5 Hz, 1H), 7.24 (m, 1H), 7.34 (m, (m, 3H), 7.79 (dd, J=1.0, 3.0 Hz, 1H).

Step B. (S)-3-(5-Chloro-2-methoxy-phenyl)-1-chloromethyl-3-fluoro-6-trifluoromethyl-1,3-dihydro-indol-2-one ((S)-V)

To a solution of (S)-3-(5-chloro-2-methoxy-phenyl)-3-fluoro-1-hydroxymethyl-6-trifluoromethyl-1,3-dihydro-indol-2-one ((S)-IV) (64.5 g, 0.166 mol) in CH$_2$Cl$_2$ (700 mL) was added PCl$_3$ (2.0 M in CH$_2$Cl$_2$, 255.0 mL, 0.510 mol) dropwise at 0° C. under N$_2$ over a period of 50 minutes. The resultant mixture was warmed to room temperature and the stirring continued overnight (16 h). The mixture was quenched with ice at 0° C. and the resultant mixture was stirred vigorously for 30 minutes. The organic layer was separated and the aqueous layer was washed with $CH_2Cl_2$. The combined organic layer was washed with brine and dried over $Na_2SO_4$. Chromatography (silica gel, EtOAc/Hexanes) provided the title compound as a white dry foam (42.0 g, 62% yield). $^1$H NMR (CDCl$_3$): δ 3.55 (s, 3H), 5.39 (d, J=10.5 Hz, 1H), 5.95 (d, J=11.0 Hz, 1H), 6.76 (dd, J=1.5, 9.0 Hz, 1H), 7.28 (m, 2H), 7.35 (dd, J=1.5, 9.0 Hz, 1H), 7.40 (d, J=8.0 Hz, 1H), 7.78 (dd, J=1.0, 2.5 Hz, 1H).

Step C. (S)-Phosphoric acid mono-[3-(5-chloro-2-methoxyphenyl)-3-fluoro-2-oxo-6-trifluoromethyl-2,3-dihydro-indol-1-ylmethyl] ester, mono tetrabutylammonium salt; (S)-Ia'

The $H_2O$ in the commercially available tetrabutylammonium dihydrogen phosphate (Aldrich, 1.0 M, 1000 mL, 1.0 mol) was removed by evaporation at 28° C. and dried overnight at high vacuum. The residue was redissolved in dried acetonitrile (4A, 2500 mL). To this solution was added a solution of (S)-3-(5-chloro-2-methoxy-phenyl)-1-chloromethyl-3-fluoro-6-trifluoromethyl-1,3-dihydro-indol-2-one ((S)-V) (42.0 g, 0.103 mol) in $CH_3CN$ (200 mL) dropwise at 0° C. under $N_2$ over a period of 30 minutes. The reaction mixture was stirred at 0° C. for another 30 minutes. The stirring continued at room temperature for 2.5 hours and the solvent was removed. The residue was dissolved in $CH_2Cl_2$ (1200 mL), washed with $H_2O$ (4×200 mL) and dried over $Na_2SO_4$. Chromatography (silica gel, MeOH/$CH_2Cl_2$) provided the title compound as a white solid (28.0 g, 38% yield). LC/MS m/e: 470 (MH$^+$), 99% purity. $^1$H NMR ($D_2O$): δ 0.89 (t, J=7.4 Hz, 12H), 1.29 (m, 8H), 1.58 (m, 8H), 3.11 (t, J=7.3 Hz, 8H), 3.44 (s, 3H), 5.48 (m, 1H), 5.59 (m, 1H), 6.80 (d, J=9.0 Hz, 1H), 6.98 (d, J=7.0 Hz, 1H), 7.16 (d, J=7.5 Hz, 1H), 7.26 (d, J=8.5 Hz, 1H), 7.66 (s, 1H), 7.71 (s, 1H).

EXAMPLE 3

(S)-Phosphoric acid mono-[3-(5-chloro-2-methoxy-phenyl)-3-fluoro-2-oxo-6-trifluoromethyl-2,3-dihydro-indol-1-ylmethyl] ester, mono sodium salt; (S)-Ia$^2$ Dowex-50wx8-100 resin (1350 g) was washed with $H_2O$, MeOH, $H_2O$, and then basified to pH>10 with sodium hydroxide solution (1.0M). It was then washed with $H_2O$ to pH~7 and the resin was divided into three portions (~450 g each). To a solution of (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt; (S)-Ia$^1$: (27 g, 0.038 mol) in 500 mL of $H_2O$ was added one portion of resin (~450 g). The mixture was stirred for 10 minutes, filtered and washed with $H_2O$. To the combined filtrate was added another portion of resin. The mixture was stirred for 10 minutes, filtered and washed with $H_2O$. To this filtrate was added the last portion of resin. The mixture was stirred for 10 minutes, filtered and washed with $H_2O$. The combined filtrates were filtered over a short bed (1 cm) of C-18 reverse phase silica gel and washed with $H_2O$. The solvents of the combined filtrates were evaporated. The residue was dissolved in acetonitrile and filtered. The acetonitrile was evaporated, the residue was redissolved in $CH_2Cl_2$, and hexanes were added to the solution. Evaporation of the solvents provided the title compound as a white fine powder (15.4 g, 87% yield). MS m/e: 468.0 (M−H$^−$). LC/MS m/e: 470 (MH$^+$), 98% purity. Anal. Calcd. for $C_{17}H_{12}ClF_4NO_6PN \cdot 1.05Na \cdot 0.18H_2O$: C, 41.15; H, 2.51; N, 2.82, Na, 4.89. Found: C, 41.54; H, 2.50; N, 2.70; Na, 4.97. $^1$H NMR ($D_2O$): δ 3.52 (s, 3H), 5.56 (m, 1H), 5.65 (m, 1H), 6.94 (d, J=9.0 Hz, 1H), 7.21 (d, J=7.5 Hz, 1H), 7.36 (d, J=7.5 Hz, 1H), 7.43 (dd, J=1.5, 9.0 Hz, 1H), 7.72 (s, 1H), 7.79 (s, 1H). $^{13}$C NMR ($D_2O$): δ 58.79, 67.99 94.23 110.52 116.42 124.01 126.38, 128.04, 128.35, 128.49, 128.74, 131.48, 133.52, 135.98, 145.96, 156.38, 175.98. $^{19}$F NMR ($D_2O$): δ−63.2, −164. $^{31}$P NMR ($D_2O$): 60.12. 0.12. IR (KBr, cm$^{-1}$): 3433, 1756, 1319, 1131, 1026. [α]$^{20}$ ($H_2O$)+131.95. Chiral capillary electrophoresis (CE) analysis showed 99+% (S)-isomer.

EXAMPLE 4

(R)-Phosphoric acid mono-[3-(5-chloro-2-methoxy-phenyl)-3-fluoro-2-oxo-6-trifluoromethyl-2,3-dihydro-indol-1-ylmethyl] ester, monosodium salt; (R)-Ia$^2$ Starting with (R)-3-(5-chloro-2-methoxy-phenyl)-3-fluoro-6-trifluoromethyl-1,3-dihydro-indol-2-one ((R)-II) (prepared according to U.S. Pat. No. 5,602,169), the title compound was prepared using the general procedures described in Examples 2 and 3. [α]$^{20}$ ($H_2O$)−104.42. Chiral capillary electrophoresis (CE) analysis showed 89% (R)-isomer and 10% (S)-isomer along with 1% unidentified substance.

EXAMPLE 5

(S)-3-(5-Chloro-2-methoxy-phenyl)-3-fluoro-2-oxo-6-trifluoromethyl-2,3-dihydro-indole-1-carboxylic acid 2-phosphonooxy-propyl ester; (S)-Ib, n=2)

Step A. (S)-3-(5-Chloro-2-methoxy-phenyl)-3-fluoro-2-oxo-6-trifluoromethyl-2,3-dihydro-indole-1-carboxylic acid 2-(di-tert-butoxy-phosphoryloxy)-propyl ester ((S)-VII, n=2)

To a solution of (S)-3-(5-chloro-2-methoxy-phenyl)-3-fluoro-6-trifluoromethyl-1,3-dihydro-indol-2-one ((S)-II) (720 mg, 2 mmol) in dichloromethane was dropped in phosgene (2.2 mL, 20% solution in toluene, 4 mmol) and pyridine (0.6 mL). The resulting chloroformate (S)-3-(5-chloro-2-methoxy-phenyl)-3-fluoro-2-oxo-6-trifluoromethyl-2,3-dihydro-indole-1-carbonyl chloride ((S)-VI) was stirred at room temperature under $N_2$ atmosphere over night. To this reaction mixture was dropped in another 0.6 mL of pyridine, followed by the addition of phosphoric acid di-tert-butyl ester 3-hydroxy-propyl ester (1.55 g, ~5.78 mmol), the preparation of which is given below. The resulting mixture was stirred at room temperature for another hour, was diluted with dichloromethane and washed with water. The organic layer was dried over $Na_2SO_4$ and condensed by evaporator. The residue was chromatographed on a silica gel flash column packed with ethyl acetate:hexane (v/v, 4:1) and eluted with ethyl acetate-:hexane (v/v, 4:1~2:1) to afford the title compound (818 mg, 63%). $^1$H NMR (CDCl$_3$, 500 MHz) δ 10.06 (s, 1H), 8.31 (s, 1H), 7.78 (t, 1H), 7.43 (d, 1H), 7.35 (dd, 1H), 7.27 (d, 1H), 6.76 (dd, 1H), 4.59 (m, 2H), 4.16 (m, 2H), 3.52 (s, 3H), 2.18 (m, 2H), 1.48 (s, 18H); LC-MS, 654.1 (MH$^+$).

Preparation of Phosphoric acid di-tert-butyl ester 3-hydroxy-propyl ester

To a 100 mL flask was added tetra-n-butyl ammonium phosphoric acid di-tert-butyl ester salt (3.08 g, 6.8 mmol), ethylene glycol dimethyl ether (10 mL), and 3-bromo-1-propanol (freshly distilled from potassium carbonate). The reaction mixture was heated to reflux for 2.5 hours. After cooling to room temperature, the reaction mixture was diluted with ethyl ether (60 mL) and cooled in a refrigerator until a white solid precipitated. The solid was filtered through Celite and the filtrate was evaporated in vacuo, affording the title compound as a clear oil (1.85 g, ~100%). $^1$H NMR (CDCl$_3$, 500 MHz) δ 4.10 (m, 2H), 3.73 (m, 2H), 1.84 (m, 2H), 1.46 (s, 18H).

Step B. (S)-3-(5-Chloro-2-methoxy-phenyl)-3-fluoro-2-oxo-6-trifluoromethyl-2,3-dihydro-indole-1-carboxylic acid 2-phosphonooxy-propyl ester; (S)-Ib, n=2)

A solution of (S)-3-(5-chloro-2-methoxy-phenyl)-3-fluoro-2-oxo-6-trifluoromethyl-2,3-dihydro-indole-1-carboxylic acid 2-(di-tert-butoxy-phosphoryloxy)-propyl ester ((S)-VII, n=2) (540 mg, 0.82 mmol) in dichloromethane (30 mL) was stirred with trifluoroacetic acid (0.6 mL) at room temperature for 3 hours. LC-MS indicated the completion of the reaction. After removal of the solvent the residue was dissolved in methanol and the crude product was purified by prep. HPLC, affording the title compound 255 mg (57%) as white solid after lyophilization. $^1$H NMR (CDCl$_3$, 500 MHz) δ 8.27 (s, 1H), 7.73 (d, 1H), 7.42 (d, 1H), 7.32 (d, 1H), 7.27 (d, 1H), 6.75 (d, 1H), 4.50 (b, 6H, containing some H$_2$O as solvate), 4.54 (m, 2H), 4.17 (b, 2H), 3.49 (s, 3H), 2.1 (m, 2H); MS (m/e) 539.92 (M$^+$–1); LC-MS, 542 (MH$^+$, 98.5%); $^{31}$P NMR (CDCl$_3$, 500 MHz) δ 2.03; $^{19}$F NMR (CDCl$_3$, 500 MHz) δ–63.4, 153.8; Anal. Calcd. for C$_{20}$H$_{17}$ClF$_4$NO$_8$P: C=44.34%, H=3.16%, N=2.58%; Found: C=44.01%, H=3.11%, N=2.45%.

EXAMPLE 6

(S)-3-(5-Chloro-2-methoxy-phenyl)-3-fluoro-2-oxo-6-trifluoromethyl-2,3-dihydro-indole-1-carboxylic acid 2-phosphonooxy-ethyl ester; (S)-Ib, n=1)

Step A. (S)-3-(5-Chloro-2-methoxy-phenyl)-3-fluoro-2-oxo-6-trifluoromethyl-2,3-dihydro-indole-1-carboxylic acid 2-(di-tert-butoxy-phosphoryloxy)-ethyl ester ((S)-VII, n=1)

The title compound was prepared analogously to (S)-3-(5-chloro-2-methoxy-phenyl)-3-fluoro-2-oxo-6-trifluoromethyl-2,3-dihydro-indole-1-carboxylic acid 2-(di-tert-butoxy-phosphoryloxy)-propyl ester ((S)-VII, n=2) in 52% yield, using phosphoric acid di-tert-butyl ester 2-hydroxy-ethyl ester. $^1$H NMR (CDCl$_3$, 500 MHz) δ 8.29 (s, 1H), 7.77 (d, 1H), 7.43 (d, 1H), 7.35 (d, 1H), 7.27 (d, 1H), 6.75 (d, 1H), 4.67 (m, 2H), 4.31 (m, 2H), 3.53 (s, 3H), 1.47 (s, 18H); LC-MS, 640.15 (MH$^+$, 96); $^{31}$P NMR (CDCl$_3$, 500 MHz) δ–8.71; $^{19}$F NMR (CDCl$_3$, 500 MHz) δ–63.3, 153.6.

Step B. (S)-3-(5-Chloro-2-methoxy-phenyl)-3-fluoro-2-oxo-6-trifluoromethyl-2,3-dihydro-indole-1-carboxylic acid 2-phosphonooxy-ethyl ester; (S)-Ib, n=1)

Using (S)-3-(5-chloro-2-methoxy-phenyl)-3-fluoro-2-oxo-6-trifluoromethyl-2,3-dihydro-indole-1-carboxylic acid 2-(di-tert-butoxy-phosphoryloxy)-ethyl ester ((S)-VII, n=1) as starting material, the title compound was prepared analogously to (S)-3-(5-Chloro-2-methoxy-phenyl)-3-fluoro-2-oxo-6-trifluoromethyl-2,3-dihydro-indole-1-carboxylic acid 2-phosphonooxy-propyl ester; (S)-Ib, n=2) in 83%. $^1$H NMR (CDCl$_3$, 500 MHz) δ 8.23 (s, 1H), 7.73 (d, 1H), 7.45 (d, 1H), 7.30 (d, 1H), 7.28 (d, 1H), 6.75 (d, 1H), 4.59 (m, 2H), 4.33 (m, 2H), 3.51 (s, 3H); MS (m/e) 525.95 (M$^+$–1); $^{31}$P NMR (CDCl$_3$, 500 MHz) δ 1.87; $^{19}$F NMR (CDCl$_3$, 500 MHz) δ–63.25, 153.8; Anal. Calcd. for C$_{19}$H$_{15}$ClF$_4$NO$_8$P·0.159H$_2$O: C=41.60%, H=3.18%, N=2.55%; Found: C=41.57%, H=2.92%, N=2.51%.

EXAMPLE 7

(S)-(2-Phosphonooxy-ethyl)-carbamic acid 3-(5-chloro-2-methoxy-phenyl)-3-fluoro-2-oxo-6-trifluoromethyl-2,3-dihydro-indol-1-ylmethyl ester; (S)-Ic, n=1)

Step A. (S)-(2-Hydroxy-ethyl)-carbamic acid 3-(5-chloro-2-methoxy-phenyl)-3-fluoro-2-oxo-6-trifluoromethyl-2,3-dihydro-indol-1-ylmethyl ester ((S)-IX, n=1)

To a 25 mL round bottom flask containing (S)-3-(5-chloro-2-methoxy-phenyl)-3-fluoro-1-hydroxymethyl-6-trifluoromethyl-1,3-dihydro-indol-2-one ((S)-IV) (0.397 g, 1.02 mmol) was added 5 mL anhydrous dichloromethane, triethylamine (0.204 g, 2.04 mmol), and 4-nitrophenyl chloroformate (0.246 g, 1.22 mmol). The reaction was allowed to stir overnight at room temperature, affording carbonic acid 3-(5-chloro-2-methoxy-phenyl)-3-fluoro-2-oxo-6-trifluoromethyl-2,3-dihydro-indol-1-ylmethyl ester 4-nitrophenyl ester (VIII), after which 2-aminoethanol (0.186 g, 3.05 mmol) was added and the reaction was allowed to stir for an additional 24 hours. The solvent was removed in vacuo, and the crude residue was purified by column chromatography (silica gel; 1:1 Hex:EtOAc to 4:1 EtOAc:Hex) producing 0.250 g (51%) of the title compound. $^1$H NMR (CDCl$_3$ 400 MHz): δ=7.78 (s,1H), 7.51 (s, 1H), 7.33 (d, 2H, J=7 Hz), 7.22 (d, 1H, J=7 Hz), 6.74 (d, 1H, J=7 Hz), 5.88 (d, 1H, J=12 Hz), 5.83 (d, 1H, J=12 Hz), 3.75 (m, 2H), 3.50 (s, 3H), 3.39 (m, 2H, J=7 Hz).

Step B. (S)-[2-(Di-tert-butoxy-phosphoryloxy)-ethyl]-carbamic acid 3-(5-chloro-2-methoxy-phenyl)-3-fluoro-2-oxo-6-trifluoromethyl-2,3-dihydro-indol-1-ylmethyl ester ((S)-X, n=1)

To a 25 mL pear shaped flask containing (S)-(2-Hydroxy-ethyl)-carbamic acid 3-(5-chloro-2-methoxy-phenyl)-3-fluoro-2-oxo-6-trifluoromethyl-2,3-dihydro-indol-1-ylmethyl ester ((S)-IX, n=1) (0.250 g, 0.526 mmol) was added 3 mL anhydrous dichloromethane, 1H-tetrazole (0.110 g 1.58 mmol), 4-DMAP (0.026 g, 0.21 mmol), and di-t-butyl-diisopropylphosphoramidite (0.291 g, 1.05 mmol). The reaction was stirred for 2 hours at room temperature then cooled to 0° C. and 30% aq. hydrogen peroxide (0.7 mL) was added and the reaction was stirred for an additional 1 hour. The organic layer was separated, dried (Na$_2$SO$_4$) and evaporated in vacuo. The crude oil was purified by flash chromatography (silica gel 1:1 EtOAc:Hex to 2:1 EtOAc:Hex) producing 0.280 g (80%) of the title compound. $^1$H NMR (CDCl$_3$ 400 MHz): δ=7.78 (s, 1H), 7.49 (s, 1H), 7.32 (d, 2H, J=7 Hz), 7.25 (d, 1H, J=7 Hz), 6.74 (d, 1H, J=7 Hz), 5.84 (dd, 2H, 12 Hz), 4.05 (m, 2H), 3.51 (s, 3H), 3.48 (m, 2H), 1.46 (s, 9H), 1.45 (s, 9H).

Step C. (S)-(2-Phosphonooxy-ethyl)-carbamic acid 3-(5-chloro-2-methoxy-phenyl)-3-fluoro-2-oxo-6-trifluoromethyl-2,3-dihydro-indol-1-ylmethyl ester; (S)-Ic, n=1)

To a 25 mL pear shaped flask containing ester (S)-[2-(di-tert-butoxy-phosphoryloxy)-ethyl]-carbamic acid 3-(5-chloro-2-methoxy-phenyl)-3-fluoro-2-oxo-6-trifluoromethyl-2,3-dihydro-indol-1-ylmethyl ester ((S)-X, n=1) (0.280 g, 0.419 mmol) was added 5 mL anhydrous dichloromethane, and trifluoroacetic acid (0.143 g, 1.26 mmol). The reaction was stirred for 3 hours at room temperature, the organic layer was evaporated in vacuo and the crude foam was placed under high vacuum overnight. The resulting white powder was purified by reverse phase chromatography (C$_{18}$; 1:1 CH$_3$CN:H$_2$O) producing the title compound (0.134 g, 58%) as a white powder. $^1$H NMR (D$_2$O 400 MHz): δ=7.88 (s, 1H), 7.74 (s, 1H), 7.50 (m, 2H), 7.40 (d, 1H, J=7 Hz), 7.00 (d, 1H, J=7 Hz), 5.99 (d, 1H, J=12 Hz), 5.77 (d, 1H, J=12 Hz), 3.90 (m, 2H), 3.48 (s, 3H), 3.39 (m, 2H); LRMS [M–H]$^-$554.91, [M+NH$_4$]$^+$574.0.

EXAMPLE 8

(S)-Phosphonooxy-acetic acid 3-(5-chloro-2-methoxy-phenyl)-3-fluoro-2-oxo-6-trifluoromethyl-2,3-dihydro-indol-1-ylmethyl ester; (S)-Id, n=1)

Step A. (S)-Hydroxy-acetic acid 3-(5-chloro-2-methoxy-phenyl)-3-fluoro-2-oxo-6-trifluoromethyl-2,3-dihydro-indol-1-ylmethyl ester ((S)-XI)

To a 10 mL flask containing (S)-3-(5-chloro-2-methoxy-phenyl)-1-chloromethyl-3-fluoro-6-trifluoromethyl-1,3-dihydro-indol-2-one ((S)-V) (0.200 g, 0.489 mmol) was added 3 mL anhydrous acetonitrile, glycolic acid (0.045 g, 0.588 mmol) and cesium carbonate (0.079 g, 0.245 mmol). The reaction was stirred for 36 hours at room temperature, then the organic layer was diluted with 5 mL diethyl ether and the organic solution was decanted away from the solid cesium chloride. The solvent was evaporated in vacuo and the resulting white foam was purified by flash chromatography (silica gel 4:1 hexanes:acetone) producing the title compound (0.126 g, 58%) as a white powder. $^1$H NMR (CDCl$_3$ 400 MHz): δ=7.79 (s, 1H), 7.38–7.33 (m, 3H), 7.26 (d, 1H, J=7 Hz), 6.75 (d, 1H, J=7 Hz), 5.99 (d, 1H, J=12 Hz), 5.91 (d, 1H, J=12 Hz), 4.26 (s, 2H), 3.49 (s, 3H).

Step B. (Di-tert-butoxy-phosphoryloxy)-acetic acid 3-(5-chloro-2-methoxy-phenyl)-3-fluoro-2-oxo-6-trifluoromethyl-2,3-dihydro-indol-1-ylmethyl ester ((S)-XII)

To a 25 mL flask containing (S)-hydroxy-acetic acid 3-(5-chloro-2-methoxy-phenyl)-3-fluoro-2-oxo-6-trifluoromethyl-2,3-dihydro-indol-1-ylmethyl ester ((S)-XI) (0.126 g, 0.282 mmol) was added 3 mL anhydrous dichloromethane, 1H-tetrazole (0.059 g, 0.846 mmol), 4-dimethylaminopyridine (0.0138 g, 0.113 mmol), and di-t-butyl-diisopropylphosphoramidite (0.156 g, 0.560 mmol). The reaction was allowed to stir at room temperature for 2 hours, then the reaction was cooled to 0° C. and 30% hydrogen peroxide (0.8 mL) was added and the reaction was vigorously stirred for an additional 2 hours. The organic layer was separated, washed with distilled water, dried (Na$_2$SO$_4$) and evaporated in vacuo. The crude foam was purified by flash chromatography (silica gel 4:1 Hexanes:EtOAc) producing the title compound (0.144 g, 80%) as a white powder. $^1$H NMR (CDCl$_3$ 400 MHz): δ=7.78 (s, 1H), 7.36–7.33 (m, 3H), 7.26 (d, 1H, J=7 Hz), 6.75 (d, 1H, J=7 Hz), 5.99 (d, 1H, J=12 Hz), 5.89 (d, 1H, J=12 Hz), 4.58 (d, 2H, J=8.6 Hz), 3.52 (s, 3H), 1.47 (s, 18H).

Step C. (S)-Phosphonooxy-acetic acid 3-(5-chloro-2-methoxy-phenyl)-3-fluoro-2-oxo-6-trifluoromethyl-2,3-dihydro-indol-1-ylmethyl ester; (S)-Id, n=1)

To a 25 mL flask containing (S)-hydroxy-acetic acid 3-(5-chloro-2-methoxy-phenyl)-3-fluoro-2-oxo-6-trifluoromethyl-2,3-dihydro-indol-1-ylmethyl ester ((S)-XI) (0.144 g, 0.225 mmol) was added 4 mL anhydrous dichloromethane, and trifluoroacetic acid (0.077 g, 0.675 mmol). The reaction was allowed to stir at room temperature for 3 hours. The dichloromethane was evaporated in vacuo, and the crude foam was purified by reverse phase chromatography (C$_{18}$ 1:1CH$_3$CN:H$_2$O) producing the title compound (0.075 g, 63%) as a white powder. $^1$H NMR (CD$_3$OD 400 MHz): δ=7.73 (s, 1H), 7.74 (s, 1H), 7.62 (s, 1H), 7.43–7.40 (m, 2H), 7.33 (d, 1H, J=7 Hz), 6.95 (d, 1H, J=7 Hz), 6.05 (d, 1H, J=11.2 Hz), 5.96 (d, 1H, J=11.2 Hz), 4.62 (d, 2H, J=9.6 Hz), 3.52 (s, 3H); $^{31}$P NMR (CD$_3$OD 162 MHz) δ=0.89; $^{19}$F NMR (CD$_3$OD 376 MHz) δ=−64.7, −160.9; LRMS [M−H]$^-$525.84, [M+NH$_4$]$^+$545.0.

EXAMPLE 9

(S)-3-(5-Chloro-2-methoxy-phenyl)-3-fluoro-2-oxo-6-trifluoromethyl-2,3-dihydro-indole-1-carboxylic acid phosphonooxymethyl ester; (S)-Ie)

Step A. (S)-3-(5-Chloro-2-methoxy-phenyl)-3-fluoro-2-oxo-6-trifluoromethyl-2,3-dihydro-indole-1-carboxylic acid chloromethyl ester, (S)-XII)

To a 10 mL flask containing (S)-3-(5-chloro-2-methoxy-phenyl)-3-fluoro-2-oxo-6-trifluoromethyl-1,3-dihyrdro-indol-2-one(S)-II(0.400 g, 1.1 mmol) was added 6 mL anhydrous dichloromethane, triethylamine (0.167 g, 1.67 mmol) and chloromethylchloroformate (0.171 g, 1.33 mmol). The reaction was stirred for 24 hours at room temperature, then the organic layer was diluted with 75 mL diethyl ether and the solid triethylamine hydrochloride was filtered off through Celite. The solvent was evaporated in vacuo and the title compound (0.414 g, 83%) was used in subsequent reactions without purification. $^1$H NMR (CDCl$_3$ 400 MHz): δ=8.36 (s, 1H), 7.79 (s, 1H), 7.49 (d, 1H, J=7 Hz), 7.36 (d, 1H, J=7 Hz), 7.34 (d, 1H, J=7 Hz), 6.77 (d, 1H, J=7 Hz), 6.10 (d, 1H, J=6.4 Hz), 5.96 (d, 1H, J=6.4 Hz), 3.56 (s, 3H).

Step B: 3-(5-Chloro-2-methoxy-phenyl)-3-fluoro-2-oxo-6-trifluoromethyl-2,3-dihydro-indole-1-carboxylic acid iodomethyl ester ((S)-XIV)

To a 25 mL flask containing (S)-3-(5-chloro-2-methoxy-phenyl)-3-fluoro-2-oxo-6-trifluoromethyl-2,3-dihydro-indole-1-carboxylic acid chloromethyl ester ((S)-XII) (0.633 g, 1.40 mmol) was added 6 mL anhydrous acetone, and sodium iodide (0.314 g, 2.10 mmol). The reaction was heated to reflux and stirred for 4 hours, then the reaction was cooled to room temperature, and the solvent was evaporated in vacuo. The crude oil was dissolved in dichloromethane and washed with a 1% aq. sodium thiosulfate solution. The organic layer was separated, dried (Na$_2$SO$_4$) and evaporated in vacuo producing the title compound (0.640 g, 84%) which was used in subsequent reactions without purification. $^1$H NMR (CDCl$_3$ 400 MHz): δ=8.38 (s, 1H), 7.78 (s, 1H), 7.48 (d, 1H, J=7 Hz), 7.36 (d, 1H, J=7 Hz), 7.31 (d, 1H, J=7 Hz), 6.77 (d, 1H, J=7 Hz), 6.28 (d, 1H, J=6.4 Hz), 6.18 (d, 1H, J=6.4 Hz), 3.56 (s, 3H).

Step C: (S)-3-(5-Chloro-2-methoxy-phenyl)-3-fluoro-2-oxo-6-trifluoromethyl-2,3-dihydro-indole-1-carboxylic acid di-tert-butoxy-phosphoryloxymethyl ester ((S)-XV)

To a 25 mL flask containing 3-(5-chloro-2-methoxy-phenyl)-3-fluoro-2-oxo-6-trifluoromethyl-2,3-dihydro-indole-1-carboxylic acid iodomethyl ester ((S)-XIV) (0.200 g, 0.368 mmol) was added 5 mL anhydrous tetrahydrofuran, and tetrabutylammonium di-t-butylphosphate (0.199 g, 0.441 mmol). The reaction was heated to reflux and allowed to stir for 1 hour. The reaction was then cooled to room temperature, and the solvent was evaporated in vacuo. The crude foam was purified by flash chromatography (silica gel 4:1 Hexanes: EtOAc) producing the title compound (0.110 g, 48%) as a clear colorless oil. $^1$H NMR (CDCl$_3$ 400 MHz): δ=8.35 (s, 1H), 7.78 (s, 1H), 7.48 (d, 1H, J=7 Hz), 7.34 (d, 1H, J=7 Hz), 7.30 (d, 1H, J=7 Hz), 6.76 (d, 1H, J=7 Hz), 5.90 (d, 1H, J=12.4 Hz), 3.53 (s, 3H), 1.50 (s, 18H).

Step D: (S)-3-(5-Chloro-2-methoxy-phenyl)-3-fluoro-2-oxo-6-trifluoromethyl-2,3-dihydro-indole-1-carboxylic acid phosphonooxymethyl ester; (S)-Ie)

To a 25 mL flask containing (S)-3-(5-chloro-2-methoxy-phenyl)-3-fluoro-2-oxo-6-trifluoromethyl-2,3-dihydro-indole-1-carboxylic acid di-tert-butoxy-phosphoryloxymethyl ester ((S)-XV) (0.110 g, 0.176 mmol) was added 2 mL anhydrous dichloromethane, and trifluoroacetic acid (0.060 g, 0.527 mmol). The reaction was allowed to stir at room temperature for 4 hours. The dichloromethane was evaporated in vacuo, and the crude foam was purified by reverse phase chromatography (C$_{18}$ 2:1CH$_3$CN:H$_2$O) producing the title compound (0.070 g, 78%) as a white powder. $^1$H NMR (CDCl$_3$ 400 MHz): δ=8.26 (s, 1H), 7.68 (s, 1H), 7.45 (d, 1H, J=7 Hz), 7.28–7.24 (m, 2H), 6.72 (d, 1H, J=7 Hz), 5.90–5.81 (m, 2H), 3.48 (s, 3H); $^{31}$P NMR (CDCl$_3$ 162 MHz) δ=−0.233; $^{19}$F NMR (CDCl$_3$ 376 MHz) δ=−63.3, −153.8; LRMS [M−H]$^-$511.4, [M+NH$_4$]+530.9.

EXAMPLE 10

(S)-3-Phosphonooxy-propionic acid 3-(5-chloro-2-methoxy-phenyl)-3-fluoro-2-oxo-6-trifluoromethyl-2,3-dihydro-indol-1-ylmethyl ester; (S)-If, n=1)

Step A: (S)-3-Hydroxy-propionic acid 3-(5-chloro-2-methoxy-phenyl)-3-fluoro-2-oxo-6-trifluoromethyl-2,3-dihydro-indol-1-yl methyl ester, ((S)-XVI, n=1)

To a 10 mL flask containing (S)-3-(5-chloro-2-methoxy-phenyl)-1-chloromethyl-3-fluoro-6-trifluoromethyl-1,3-dihydro-indol-2-one ((S)-V) (0.223 g, 0.546 mmol) was added 3 mL anhydrous acetonitrile, and cesium propanoate (0.182 g, 0.819 mmol). The reaction was stirred for 24 hours at room temperature. The solvent was evaporated in vacuo and the resulting white foam was purified by flash chromatography (silica gel 3:1 Hexanes:Acetone) producing the title compound (0.115 g, 46%) as a white powder. $^1$H NMR (CDCl$_3$ 400 MHz): δ=7.79 (s, 1H), 7.37–7.32 (m, 3H), 7.25 (d, 1H, J=7 Hz), 6.75 (d, 1H, J=7 Hz), 5.93 (d, 1H, J=12 Hz), 5.85 (d, 1H, J=12 Hz), 3.92 (t, 2H, J=7 Hz), 3.51 (s, 3H), 2.66 (t, 2H, J=7 Hz).

Step B: (S)-3-(Di-tert-butoxy-phosphoryloxy)-propionic acid 3-(5-chloro-2-methoxy-phenyl)-3-fluoro-2-oxo-6-trifluoromethyl-2,3-dihydro-indol-1-ylmethyl ester ((S)-XVII, n=1)

To a 25 mL flask containing (S)-3-hydroxy-propionic acid 3-(5-chloro-2-methoxy-phenyl)-3-fluoro-2-oxo-6-trifluoromethyl-2,3-dihydro-indol-1-ylmethyl ester ((S)-XVI, n=1) (0.115 g, 0.249 mmol) was added 4 mL anhydrous dichloromethane, 1H-tetrazole (0.052 g, 0.747 mmol), 4-dimethylaminopyridine (0.012 g, 0.099 mmol), and di-t-butyl-diisopropylphosphoramidite (0.138 g, 0.498 mmol). The reaction was allowed to stir at room temperature for 2 hours, then the reaction was cooled to 0° C. and 30% hydrogen peroxide (0.8 mL) was added and the reaction was vigorously stirred for an additional 2 hours. The organic layer was separated, washed with distilled water, dried (Na$_2$SO$_4$) and evaporated in vacuo. The crude foam was purified by flash chromatography (silica gel 4:1 Hexanes:EtOAc) producing the title compound (0.144 g, 88%) as a white powder. $^1$H NMR (CDCl$_3$ 400 MHz): δ=7.78 (s, 1H), 7.36–7.32 (m, 3H), 7.26 (d, 1H, J=7 Hz), 6.75 (d, 1H, J=7 Hz), 5.90 (d, 1H, J=12 Hz), 5.84 (d, 1H, J=12 Hz), 4.25 (q, 2H, J=7.6, 6.4 Hz), 3.51 (s, 3H), 2.77 (t, 2H, J=6.4 Hz), 1.46 (s, 18H).

Step C: (S)-3-Phosphonooxy-propionic acid 3-(5-chloro-2-methoxy-phenyl)-3-fluoro-2-oxo-6-trifluoromethyl-2,3-dihydro-indol-1-ylmethyl ester; (S)-If, n=1)

To a 25 mL flask containing (S)-3-(di-tert-butoxy-phosphoryloxy)-propionic acid 3-(5-chloro-2-methoxy-phenyl)-3-fluoro-2-oxo-6-trifluoromethyl-2,3-dihydro-indol-1-ylmethyl ester ((S)-XVII, n=1) (0.144 g, 0.22 mmol) was added 2 mL anhydrous dichloromethane, and trifluoroacetic acid (0.075 g, 0.66 mmol). The reaction was allowed to stir at room temperature for 4 hours. The dichloromethane was evaporated in vacuo, and the crude foam was purified by reverse phase chromatography (C$_{18}$ 2:1CH$_3$CN:H$_2$O) producing the title compound (0.070 g, 59%) as a white powder. $^1$H NMR (CDCl$_3$ 400 MHz): δ=7.70 (s, 1H), 7.36 (s, 1H), 7.32–7.27 (m, 3H), 7.20 (d, 1H, J=6 Hz), 6.73 (d, 1H, J=8 Hz), 5.91 (d, 1H, J=11.2 Hz), 5.73 (d, 1H, J=11.2 Hz), 4.27 (m, 2H), 3.44 (s, 3H), 2.75 (m, 2H); $^{31}$P NMR (CDCl$_3$ 162 MHz) δ=1.15; $^{19}$F NMR (CDCl$_3$ 376 MHz) δ=−63.2, −159.4; LRMS [M−H]$^-$539.89, [M+NH$_4$]$^+$564.1.

EXAMPLE 11

(S)-Pyrophosphoric acid 3-(5-chloro-2-methoxy-phenyl)-3-fluoro-2-oxo-6-trifluoro methyl-2,3-dihydro-indol-1-yl methyl ester, trisodium salt; (S) Ig$^2$, M+=Na$^+$)

Step A. (3S)-Pyrophosphoric acid 3-(5-chloro-2-methoxy-phenVI)-3-fluoro-2-oxo-6-trifluoro methyl-2,3-dihydro-indol-1-yl methyl ester, tris(tetrabutylammonium) salt ((S)-Ig$^1$, R=n-butyl)

A solution of (S)-3-(5-chloro-2-methoxy-phenyl)-1-chloromethyl-3-fluoro-6-trifluoromethyl-1,3-dihydro-indol-2-one ((S)-V) (0.45 g, 1.15 mmol) and tris-(tetrabutylammonium)-hydrogen pyrophosphate (1.04 g, 1.15 mmol) were mixed in CH$_3$CN (25 ml) and stirred at room temperature for approximately 45 minutes. The solvent was removed under reduced pressure and the oily residue was filtered through a plug of C-18 reverse-phase-silica gel, eluting with CH$_3$CN/H$_2$O (1:1). The solvents were removed under vacuum and the residue was purified by flash chromatography (SiO$_2$) eluting with iPrOH/NH$_4$OH (70:30) to provide the title compound as a glassy oil and used directly in the subsequent ion exchange reaction.

Step B. (S)-Pyrophosphoric acid 3-(5-chloro-2-methoxy-phenyl)-3-fluoro-2-oxo-6-trifluoro methyl-2,3-dihydro-indol-1-yl methyl ester, trisodium salt ((S)-Ig$^2$, M$^+$=Na$^+$)

The recovered glassy oil from above ((S)-pyrophosphoric acid 3-(5-chloro-2-methoxy-phenyl)-3-fluoro-2-oxo-6-trifluoro methyl-2,3-dihydro-indol-1-yl methyl ester tris (tetrabutylammonium) salt ((S)-Ig$^2$, R=n-butyl) was dissolved in deionized H$_2$O and applied to an ion-exchange resin column (DOWEX 50WX8-200, Na$^+$ form). The fractions containing the title compound were lyophilized, yielding a fluffy white solid (0.34 g, 48% over two steps) with the appearance of large thin needles. $^1$H NMR (500 MHz, D$_2$O): δ 3.58 (s, 3H), 5.67 (dd, J=6.41, 10.68 Hz, 1H), 5.78 (dd, J=7.02, 10.68 Hz, 1H), 7.01 (d, J=8.55 Hz, 1H), 7.41 (m, 1H), 7.51 (m, 2H), 7.83 (s, 1H), 789 (s, 1H). $^{31}$P NMR (200 MHz, D$_2$O)−6.86 (d, J=22.05), −11.85 (d, J=22.05). $^{19}$F NMR (470 MHz, D$_2$O)−63.0 (s), −161.7 (s) LRMS: 548 (M−3H).

EXAMPLE 12

(S)-Phosphoric acid-[3-(5-chloro-2-methoxy-phenyl)-3-fluoro-2-oxo-6-trifluoromethyl-2,3-dihydro-indol-1-ylmethyl ester] methyl ester, mono sodium salt; (S)-Ih$^2$, M$^+$=Na$^+$, R$^1$═CH$_3$)

Step A. (S)-Phosphoric acid-[3-(5-chloro-2-methoxy-phenyl)-3-fluoro-2-oxo-6-trifluoromethyl-2,3-dihydro-indol-1-ylmethyl ester] methyl ester, mono tetrabuylammonium salt ((S)-Ih$^1$, R=nBu, R$^1$═CH$_3$)

A solution of (S)-3-(5-chloro-2-methoxy-phenyl)-1-chloromethyl-3-fluoro-6-trifluoromethyl-1,3-dihydro-indol-2-one ((S)-V) (1.10 g, 2.81 mmol) and methyl bis (tetrabutylammonium) phosphate hexahydrate (1.97 g, 2.81 mmol (prepared according to: Julia, M; Mestdagh, H.; Rolando, G. *Tettrahedron*, 1986, 42, 3841–3849) were mixed in CH$_3$CN (60 ml) and stirred at room temperature for approximately 30 minutes. The solvent was removed under reduced pressure and the oily residue was purified by flash chromatography (SiO$_2$) eluting with iPrOH/NH$_4$OH (95:05) to afford the title compound as a glassy oil which was employed directly in the subsequent ion exchange reaction.

Step B. (S)-Phosphoric acid-[3-(5-chloro-2-methoxy-phenyl)-3-fluoro-2-oxo-6-trifluoromethyl-2,3-dihydro-indol-1-ylmethyl ester] methyl ester, mono sodium salt; (S)-Ih$^2$, M$^+$=Na$^+$, R$^1$═CH$_3$)

The ammonium salt described above ((S)-phosphoric acid-3-(5-chloro-2-methoxy-phenyl)-3-fluoro-2-oxo-6-trifluoromethyl-2,3-dihydro-indol-1-ylmethyl ester methyl ester mono tetrabutylammonium salt ((S)-Ih$^1$, R=nBu, R$^1$═CH$_3$)) was dissolved in deionized H$_2$O and applied to an ion-exchange resin column (DOWEX 50WX8–200, Na$^+$ form). The fractions containing the title compound were lyophilized, yielding a white solid (1.02 g, 72% over two steps). The proton NMR spectra was found to be concentration dependant. $^1$H NMR (500 MHz, $D_2O$, <<10 mg/mL): δ 3.56 (s, 3H), 3.57 (d, J=10.99 Hz, 3H), 5.51 (dd, J=7.32, 10.68 Hz, 1H), 5.58 (dd, J=7.32, 10.68 Hz, 1H), 7.02 (d, J=8.85 Hz, 1H), 7.44 (m, 1H), 7.51 (dd, J=2.44, 8.85 Hz, 1H), 7.54 (d, J=7.33 Hz, 1H), 7.72 (s, 1H) 7.90 (s, 1H). $^1$H NMR (500 MHz, $D_2O$, >10 mg/mL): δ 3.39 (s, 3H), 3.46 (d, J=10.38 Hz, 3H), 5.51 (dd, J=7.02, 10.38 Hz, 1H), 5.58 (dd, J=7.02, 10.38 Hz, 1H), 6.75 (d, J=8.55 Hz, 1H), 6.92 (bs, 1H), 7.05 (bs, 1H), 7.24 (d, J=1.83, 8.55 Hz, H), 7.60 (m, 2H). 3P NMR (200 MHz, $D_2O$) 0.95 (multiplet). $^{19}$F NMR (470 MHz, $D_2O$)−63.3 (s), −160.7 (s) LRMS: 482 (M−H).

EXAMPLE 13

(S)-Phosphoric acid-[3-(5-chloro-2-methoxy-phenyl)-3-fluoro-2-oxo-6-trifluoromethyl-2,3-dihydro-indol-1-ylmethyl ester] ethyl ester, mono sodium salt; (S)-Ih$^2$, M$^+$=Na$^+$, R$^1$=CH$_2$CH$_3$)

Step A. (S)-Phosphoric acid-[3-(5-chloro-2-methoxy-phenyl)-3-fluoro-2-oxo-6-trifluoromethyl-2,3-dihydro-indol-1-ylmethyl ester] ethyl ester, mono tetrabutylammonium salt ((S)-Ih$^1$, R=nBu, R$^1$=CH$_2$CH$_3$)

A solution of (S)-3-(5-chloro-2-methoxy-phenyl)-1-chloromethyl-3-fluoro-6-trifluoromethyl-1,3-dihydro-indol-2-one ((S)-V) (1.0 g, 2.57 mmol) and ethyl bis (tetrabutylammonium) phosphate hexahydrate (1.84 g, 2.57 mmol (prepared according to: Julia, M; Mestdagh, H.; Rolando, G. *Tetrahedron*, 1986, 42, 3841–3849) were mixed in CH$_3$CN (60 ml) and stirred at room temperature for approximately 30 minutes. The solvent was removed under reduced pressure and the oily residue was purified by flash chromatography (SiO$_2$) eluting with iPrOH/NH$_4$OH (98:02) to afford the title compound as a glassy oil which was employed directly in the subsequent ion exchange reaction.

Step B. (S)-Phosphoric acid-[3-(5-chloro-2-methoxy-phenyl)-3-fluoro-2-oxo-6-trifluoromethyl-2,3-dihydro-indol-1-ylmethyl ester] ethyl ester, mono sodium salt; (S)-Ih$^2$, M$^+$=Na$^+$, R$^1$=CH$_2$CH$_3$)

The ammonium salt described above ((S)-phosphoric acid-3-(5-chloro-2-methoxy-phenyl)-3-fluoro-2-oxo-6-trifluoromethyl-2,3-dihydro-indol-1-ylmethyl ester ethyl ester mono tetrabutylammonium salt ((S)-Ih$^1$, R=nBu, R$^1$=CH$_2$CH$_3$)) was dissolved in deionized H$_2$O and applied to an ion-exchange resin column (DOWEX 50WX8-200, Na$^+$ form). The fractions containing the title compound were lyophilized, yielding a white solid (0.89 g, 65%). $^1$H NMR (500 MHz, $D_2O$): δ 1.20 (t, J=7.02 Hz, 3H), 3.56 (s, 3H), 3.93 (m, 2H), 5.65 (m, 2H), 7.02 (d, J=8.85 Hz, 1H), 7.40 (m, 1H), 7.51 (bd, J=7.33 Hz, 2H), 7.72 (s, 1H) 7.89 (s, 1H). $^{31}$P NMR (200 MHz, $D_2O$) 0.03 (multiplet). $^{19}$F NMR (470 MHz, $D_2O$)−63.1 (s), −161.1 (s) LRMS: 496 (M−H).

EXAMPLES 14–24

General Procedure for the Preparation of Salts

The Dowex-50wx8-100 resin was washed with H$_2$O, MeOH, H$_2$O again as instructed by the manufacturer (Aldrich), it is basified to pH>10 with sodium (or tetramethylammonium) hydroxide solution (or treated with aminoacid or organic amines), and then washed with H$_2$O. The resin which is ready to use was first divided into three equal portions. To a solution of (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt in H$_2$O was added one portion of resin. The mixture was stirred for 10 minutes, filtered and washed with H$_2$O. To the combined filtrate was added another portion of resin. The mixture was stirred for 10 minutes, filtered and washed with H$_2$O. To this filtrate was added the last portion of resin. The mixture was stirred for 10 minutes, filtered and washed with H$_2$O. The solvents of the combined filtrates were evaporated. The residue was dissolved in acetonitrile and filtered to remove traces of insoluble material. Acetonitrile was evaporated. The residue was redissolved in CH$_2$Cl$_2$. Hexanes were added. Evaporation of the solvents provided the desired product as a white fine powder.

EXAMPLE 14

(S)-Phosphoric acid mono-[3-(5-chloro-2-methoxy-phenyl)-3-fluoro-2-oxo-6-trifluoromethyl-2,3-dihydro-indol-1-ylmethyl] ester, potassium salt; (S)-Ia$^2$ Following the general procedure above, 40 g Dowex-50wx8-100 resin was used to prepare 0.27 g of potassium salt (white powder) (95% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (0.40 g, 0.56 mmol). MS m/e: 468.0 (M−H$^−$). LC/MS m/e: 469.9 (MH$^+$), 1.52 min. >95% purity. Anal. Calcd. for C$_{17}$H$_{12}$ClF$_4$NO$_6$PN.1.10K.0.45H$_2$O: C, 39.27; H, 2.50; N, 2.69, K, 8.31. Found: C, 39.41; H, 2.62; N, 2.51; K, 8.43. $^1$H NMR (D$_2$O): δ 3.56 (s, 3H), 5.55 (m, 1H), 5.61 (m, 1H), 7.00 (d, J=8.5 Hz, 1H), 7.40 (d, J=7.0 Hz, 1H), 7.49 (m, 2H), 7.77 (s, 1H), 7.88 (s, 1H). $^{19}$F NMR (D$_2$O): δ−63.1, −161.7. $^{31}$P NMR (D$_2$O): δ 1.27.

EXAMPLE 15

(S)-Phosphoric acid mono-[3-(5-chloro-2-methoxy-phenyl)-3-fluoro-2-oxo-6-trifluoromethyl-2,3-dihydro-indol-1-ylmethyl] ester, tetramethylammonium salt; (S)-Ia$^2$ Following the general procedure above, 20 g Dowex-50wx8-100 resin was used to prepare 0.153 g of tetramethylammonium salt (white powder) (93% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (0.20 g, 0.28 mmol). MS m/e: 468.1 (M−H$^−$). LC/MS m/e: 470.0 (MH$^+$), 1.35 min. >95% purity. Anal. Calcd. for C$_{17}$H$_{12}$ClF$_4$NO$_6$PN·1.6C$_4$H$_{12}$N·0.8H$_2$O: C, 46.7; H, 5.50; N, 6.05. Found: C, 47.03; H, 5.84; N, 5.74. $^1$H NMR (D$_2$O): δ 3.14 (s, 19.2H), 3.52 (s, 3H), 5.50 (m, 1H), 5.53 (m, 1H), 6.96 (d, J=9.0 Hz, 1H), 7.40 (m, 1H), 7.45 (m, 2H), 7.75 (s, 1H), 7.84 (s, 1H). IR (KBr, cm$^{−1}$): 3429, 1752, 1319, 1129.

EXAMPLE 16

(S)-Phosphoric acid mono-[3-(5-chloro-2-methoxy-phenyl)-3-fluoro-2-oxo-6-trifluoromethyl-2,3-dihydro-indol-1-ylmethyl] ester, glycine salt; (S)-Ia$^2$ Following the general procedure above, 20 g Dowex-50wx8-100 resin and glycine (7.5 g) were used to prepare 0.156 g of glycine salt (white powder) (94% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (0.20 g, 0.28 mmol). MS m/e: 468.0 (M−H$^−$). Anal. Calcd. for C$_{17}$H$_{12}$ClF$_4$NO$_6$PN·1.42C$_2$H$_6$NO$_2$·0.80H$_2$O: C, 40.31; H, 3.77; N, 5 Found: C, 40.57; H, 3.59; N, 5.41. $^1$H NMR (D$_2$O): δ 3.58 (s, 3H), 3.65 (s, 2.8H), 5.63 (m, 1H), 5.71 (m, 1H), 7.03 (d, J=9.0 Hz, 1H), 7.42 (d, J=7.0, 1H), 7.52 (m, 2H), 7.75 (s, 1H), 7.92 (s, 1H). IR (KBr, cm$^{-1}$): 3431, 1759, 1319, 1131, 1023.

EXAMPLE 17

(S)-Phosphoric acid mono-[3-(5-chloro-2-methoxy-phenyl)-3-fluoro-2-oxo-6-trifluoromethyl-2,3-dihydro-indol-1-ylmethyl] ester, proline salt; (S)-Ia$^2$ Following the general procedure above, 20 g Dowex-50wx8-100 resin and proline (11.3 g) were used to prepare 0.160 g of proline salt (white powder) (97% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (0.20 g, 0.28 mmol). MS m/e: 468.1 (M–H$^-$). LC/MS m/e: 470.0 (MH$^+$), 1.35 min. >95% purity. Anal. Calcd. for $C_{17}H_{12}ClF_4NO_6PN \cdot 1.0C_5H_{10}NO_2$: C, 45.10; H, 3.95; N, 4.78. Found: C, 45.19; H, 3.96; N, 4.56. $^1$H NMR (D$_2$O): 61.95 (m, 2H), 2.03 (m, 1H), 2.35 (m, 1H), 3.28 (m, 1H), 3.35 (m, 1H), 3.58 (s, 3H), 4.11 (m, 1H), 5.55 (m, 1H), 5.61 (m, 1H), 6.94 (d, J=9.0 Hz, 1H), 7.34 (dd, J=2.0, 8.0, 1H), 7.44 (m, 2H), 7.66 (s, 1H), 7.82 (s, 1H). IR (KBr, cm$^{-1}$): 3431, 1757, 1319, 1131, 1026.

EXAMPLE 18

(S)-Phosphoric acid mono-[3-(5-chloro-2-methoxy-phenyl)-3-fluoro-2-oxo-6-trifluoromethyl-2,3-dihydro-indol-1-ylmethyl] ester, magnesium salt; (S)-Ia$^2$ The magnesium salt was prepared simply by Na$^+$/Mg$^{++}$ displacement. The product was marginally soluble in water but was more soluble in organic solvents. To a solution of Mg$_2$SO$_4$ (0.130 g, 1.1 mmol) in H$_2$O (3 mL) was added a solution of (S)-phosphoric acid mono-[3-(5-chloro-2-methoxy-phenyl)-3-fluoro-2-oxo-6-trifluoromethyl-2,3-dihydro-indol-1-ylmethyl] ester, mono sodium salt (sodium salt) (0.050 g, 0.070 mmol) in H$_2$O (2 mL). The mixture was stirred at room temperature for 10 minutes. The precipitate was filtered, washed with H$_2$O, and then dissolved in EtOAc. The residue from evaporation of solvent was re-dissolved in CH$_2$Cl$_2$ and hexanes. Evaporation of solvent provided the desired product as a white powder (0.035 g, 72% yield). MS m/e: 468.0 (M–H$^-$). LC/MS m/e: 469.9 (MH$^+$), 1.52 min. >95% purity. Anal. Calcd. for $C_{17}H_{12}ClF_4NO_6PN \cdot 0.49Mg \cdot 1.0H_2O$: C, 40.95; H, 2.83; N, 2.81; Mg, 2.39. Found: C, 40.87; H, 3.04; N, 2.44; Mg, 2.42. $^1$H NMR (D$_2$O): δ 3.54 (s, 3H), 5.50 (d, J=5.0 Hz, 1H), 5.52 (d, J=5.0 Hz, 1H), 6.99 (d, J=7.5 Hz, 1H), 7.34 (d, J=7.0 Hz, 1H), 7.47 (m, 2H), 7.78 (s, 1H), 7.86 (s, 1H). IR (KBr, cm$^{-1}$): 3433, 1757, 1319, 1132, 1025.

EXAMPLE 19

(S)-Phosphoric acid mono-[3-(5-chloro-2-methoxy-phenyl)-3-fluoro-2-oxo-6-trifluoromethyl-2,3-dihydro-indol-1-ylmethyl] ester, ammonium salt; (S)-Ia$^2$ Following the general procedure above, 50 g Dowex-50wx8-100 resin was used to prepare 0.6 g of ammonium salt (white powder) (87.8% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (1.0 g, 1.4 mmol). MS m/e: 468.1 (M–H)$^-$. LC/MS m/e: 486.8 (MH$^+$), 4.54 min. >95% purity.

Anal. Calcd. for $C_{17}H_{12}ClF_4NO_6PN \cdot 1.0NH_4 \cdot 0.35H_2O$: C, 41.43; H, 3.39; N, 5.69. Found: C, 41.41; H, 3.32; N, 5.71. $^1$H NMR (CD$_3$CN): 3.47 (s, 3H), 5.61 (d, J=6.5 Hz, 2H), 5.95(b, 2H), 6.83(d, J=8.8 Hz, 1H), 7.31 (d, J=7.8 hz, 1H), 7.36 (m, 2H), 7.64 (s,1H), 7.72 (s, 1H), 8.1 (b, 2H).

EXAMPLE 20

(S)-Phosphoric acid mono-[3-(5-chloro-2-methoxy-phenyl)-3-fluoro-2-oxo-6-trifluoromethyl-2,3-dihydro-indol-1-ylmethyl] ester, lithium salt; (S)-Ia$^2$ Following the general procedure above, the Dowex-50wx8-100 resin (50 g) was used to prepare 0.2 g of lithium salt (white powder) (78.8% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (0.3 g, 0.42 mmol). MS m/e: 468.1 (M–H)$^-$. LC/MS m/e: 486.8 for [(M$^-$)+NH$_4$]$^+$, 4.48 min. >95% purity. Anal. Calcd. for $C_{17}H_{12}ClF_4NO_6PN \cdot 1.1Li \cdot 1.2H_2O$: C, 40.93; H, 2.93; N, 2.81; Li, 1.40. Found: C, 41.01; H, 2.94; N, 2.81; Li, 1.54. $^1$H NMR (D$_2$O): 3.52 (s, 3H), 5.55 (m, 1H), 5.62 (m, 1H), 6.96(d, J=9.0 Hz, 1H), 7.30(d, J=7.5 Hz, 1H), 7.44 (m, 2H), 7.73 (s, 1H), 7.82 (s, 1H).

EXAMPLE 21

(S)-Phosphoric acid mono-[3-(5-chloro-2-methoxy-phenyl)-3-fluoro-2-oxo-6-trifluoromethyl-2,3-dihydro-indol-1-ylmethyl] ester, methanammonium salt; (S)-Ia$^2$ Following the general procedure above, the Dowex-50wx8-100 resin (15 g) was used to prepare 0.15 g of methanammonium salt (white powder) (71.1% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (0.3 g, 0.42 mmol). MS m/e: 468.11 (M–H)$^-$, LC/MS m/e: 468.11 (M–H)$^-$, 4.55 min. >95% purity. Anal. Calcd. for $C_{17}H_{12}ClF_4NO_6PN \cdot 1.0CH_6N \cdot 0.29H_2O$: C, 42.74; H, 3.68; N, 5.54. Found: C, 42.38; H, 3.65; N, 5.49. $^1$H NMR (D$_2$O): 2.57 (s, 3H), 3.47 (s, 3H), 5.53 (m, 1H), 5.56 (m, 1H), 6.88(d, J=8.8 Hz, 1H), 7.17(d, J=6.4 Hz, 1H), 7.31 (d, J=7.2 Hz, 1H), 7.37(d, J=8.0 Hz, 1H), 7.67 (s, 1H), 7.74 (s, 1H).

EXAMPLE 22

(S)-Phosphoric acid mono-[3-(5-chloro-2-methoxy-phenyl)-3-fluoro-2-oxo-6-trifluoromethyl-2,3-dihydro-indol-1-ylmethyl] ester, cyclohexylammonium salt; (S)-Ia$^2$ Following the general procedure above, the Dowex-50wx8-100 resin (25 g) was used to prepare 0.36 g of cyclohexylammonium salt (white powder) (91.6% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (0.5 g, 0.70 mmol). MS m/e: 487.1 for [(M$^-$)+NH$_4$]+. LC/MS m/e: 467.99 (M–H)$^-$, 3.82 min. >95% purity. Anal. Calcd. for $C_{17}H_{12}ClF_4NO_6PN \cdot 1.0C_6H_{14}N$: C, 48.56; H, 4.60; N, 4.92;. Found: C, 48.80; H, 4.80; N, 4.90; $^1$H NMR (D$_2$O): 1.14 (m, 1H), 1.31 (m, 4H), 1.62 (m, 1H), 1.77 (m, 2H), 1.96 (m, 2H), 3.12 (m, 1H), 3.54 (s, 3H), 5.52 (m, 1H), 5.57 (m, 1H), 6.95(d, J=9.0 Hz, 1H), 7.36(m, 1H), 7.47 (m, 2H), 7.75 (s, 1H), 7.85 (s, 1H).

EXAMPLE 23

(S)-Phosphoric acid mono-[3-(5-chloro-2-methoxy-phenyl)-3-fluoro-2-oxo-6-trifluoromethyl-2,3-dihydro-indol-1-ylmethyl] ester, piperidinium salt; (S)-Ia$^2$ Following the general procedure above, the Dowex-50wx8-100 resin (20 g) was used to prepare 0.25 g of piperidinium salt (white powder) (78.2% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (0.4 g, 0.56 mmol). MS m/e: 487.1 for [(M$^-$)+NH$_4$]+. LC/MS m/e: 467.99 (M–H)$^-$, 3.65 min. >95% purity. Anal. Calcd. for C$_{17}$H$_{12}$ClF$_4$NO$_6$PN·1.0C$_5$H$_{12}$N·0.55CH$_3$Cl·0.45H$_2$O: C, 43.16; H, 3.93; N, 4.46;. Found: C, 42.99; H, 4.18; N, 4.53; $^1$H NMR (D$_2$O): 1.64 (m, 2H), 1.76 (m, 4H), 3.13 (m, 2H), 3.53 (s, 3H), 5.55 (m, 1H), 5.61 (m, 1H), 6.98(d, J=9.0 Hz, 1H), 7.35(d, J=7.5 Hz, 1H), 7.47 (d, J=7.5 Hz, 2H), 7.73 (s, 1H), 7.85 (1H).

EXAMPLE 24

(S)-Phosphoric acid mono-[3-(5-chloro-2-methoxy-phenyl)-3-fluoro-2-oxo-6-trifluoromethyl-2,3-dihydro-indol-1-ylmethyl] ester, dimethylammonium salt; (S)-Ia$^2$ Following the general procedure above, the Dowex-50wx8-100 resin (15 g) was used to prepare 0.20 g of dimethylammonium salt (white powder) (78.9% yield) from (S)-phosphoric acid mono-[3-(5-chloro-2-methoxy-phenyl)-3-fluoro-2-oxo-6-trifluoromethyl-2,3-dihydro-indol-1-ylmethyl] ester, mono tetrabutylammonium salt (0.3 g, 0.42 mmol). MS m/e: 487.1 for [(M$^-$)+NH$_4$]$^+$. LC/MS m/e: 468.01 (M–H)$^-$, 3.66 min. >95% purity. Anal. Calcd. For C$_{17}$H$_{12}$ClF$_4$NO$_6$PN·1.2C$_2$H$_8$N·0.52CH$_3$Cl·0.26H$_2$O  C, 40.58; H, 3.67; N, 5.23;. Found: C, 40.30; H, 3.75; N, 5.50; $^1$H NMR (D$_2$O): 2.69(s, 6H), 3.49 (s, 3H), 5.52 (m, 1H), 5.60 (m, 1H), 6.91 (d, J=8.5 Hz, 1H), 7.25(m, 1H), 7.36 (m, 2H), 7.70 (s, 1H), 7.76 (s, 1H).

EXAMPLE 25

Phosphoric acid mono-[3-(5-chloro-2-methoxy-phenyl)-3-fluoro-2-oxo-6-trifluoromethyl-2,3-dihydro-indol-1-ylmethyl] ester, bis-[tris (hydroxymethyl)ammoniummethane] salt Step A. 3-(5-Chloro-2-methoxy-phenyl)-3-fluoro-1-methylsulfanylmethyl-6-trifluoromethyl-1,3-dihydro-indol-2-one To a 1 L, 3-necked round bottom flask equipped with an addition funnel was added 3-(5-chloro-2-methoxy-phenyl)-3-fluoro-6-trifluoromethyl-1,3-dihydro-indol-2-one (25 g, 69.8 mmol) and anhydrous THF (150 mL). The solution was cooled to 0° C. and potassium bis(trimethylsilyl)amide (0.5M in toluene, 153.6 mL, 76.8 mmol) was added over 25 minutes in order to keep the reaction temperature between 0° C. and 5° C. The reaction mixture immediately turned dark orange. The solution was allowed to warm to room temperature after which chloromethyl methylsulfide (6.39 mL, 76.8 mmol) was added. The dark brown reaction was then allowed to stir at reflux. After 3 hours, the reaction mixture contained 84% (AP) of the desired product. The reaction was allowed to reflux overnight. No further reaction took place during this period (82% AP of product after overnight stirring). The reaction mixture was then allowed to cool, and 1 N HCl (100 mL) was added slowly in order to keep the reaction temperature under 30° C. After stirring for 5 minutes, heptane (200 mL) was added and the layers were separated. The organic layer was then washed with saturated NaCl (200 mL), dried over anhydrous sodium sulfate and concentrated to yield crude product (29.3 g). The crude material was then recrystallized from heptane: THF (15:1) to provide 3-(5-chloro-2-methoxy-phenyl)-3-fluoro-1-methylsulfanylmethyl-6-trifluoromethyl-1,3-dihydro-indol-2-one as a light yellow powder (19.5 g, 67%). $^1$H NMR (CDCl$_3$, 400 MHz): δ=7.78 (dd, 1H, J=2.7, 0.9 Hz), 7.32 (m, 2H), 7.21 (m, 2H), 6.73 (dd, 1H, J=8.9, 1.2 Hz), 4.95 (d, 1H, J=14.6 Hz), 4.79 (d, 1H, J=14.6 Hz), 3.48 (s, 3H), 2.23 (s, 3H).

Step B: 3-(5-Chloro-2-methoxy-phenyl)-1-chloromethyl-3-fluoro-6-trifluoromethyl-1,3-dihydro-indol-2-one To a round bottomed flask equipped with stirrer and nitrogen inlet was charged 82 grams (0.195 mol) of 3-(5-chloro-2-methoxy-phenyl)-3-fluoro-1-methylsulfanylmethyl-6-trifluoromethyl-1,3-dihydro-indol-2-one from Step A and dichloromethane (500 mL). The solution was cooled 0° C. and chlorine gas was bubbled into the solution at a flow rate of about 50 mL/minute keeping the temperature of the reaction mixture in between 0–3° C. After about 90 minutes of chlorine bubbling (about 1 equivalent of chlorine). The progress of the reaction was followed by inline Raman spectroscopy, HPLC and gas mass flow meter. After the completion of the reaction, the mixture is warmed to room temperature and used as is in Step C. $^1$H NMR: (300 MHz, DMSO-d$_6$) δ 7.88 (s, 1H), 7.69 (d, J=2.3, 1H), 7.49 (dd, J=2.6, 8.8, 1H), 7.41 (s, 1H), 7.04 (dd, J=1.2, 8.9, 1H), 5.40 (d, J=5.9, 2H), 5.25 (bs, 12H), 3.52 (s, 3H), 3.35 (s, 12H), 2.15 (s, 4.4H, acetone peak).

Alternate Method: Sulfuryl chloride (135 mg, 80.2 μL, 1 mmol) was added at room temperature to a dichloromethane (10 mL) solution of 3-(5-chloro-2-methoxy-phenyl)-3-fluoro-1-methylsulfanylmethyl-6-trifluoromethyl-1,3-dihydro-indol-2-one (420 mg, 1 mmol) in a round-bottomed flask equipped with nitrogen inlet and magnetic stirrer. After stirring the reaction mixture at room temperature for 20 minutes, the crude solution was concentrated in vacuo to afford 3-(5-chloro-2-methoxy-phenyl)-1-chloromethyl-3-fluoro-6-trifluoromethyl-1,3-dihydro-indol-2-one (425 mg, 100% crude yield) as a light yellow solution.

Step C: Phosphoric acid mono-[3-(5-chloro-2-methoxy-phenyl)-3-fluoro-2-oxo-6-trifluoromethyl-2,3-dihydro-indol-1-ylmethyl] ester, bis-[tris(hydroxymethyl) ammoniummethane] salt The solution from Step B containing 3-(5-chloro-2-methoxy-phenyl)-1-chloromethyl-3-fluoro-6-trifluoromethyl-1,3-dihydro-indol-2-one was added into a stirred dichloromethane (1500 mL) solution of tetra-n-butyl ammonium dihydrogenphosphate (801 g) at 40° C. over a period of about 90 minutes. The resulting clear solution was stirred at 40° C. for 10 minutes to complete the reaction.

A portion of the above solution (160 mL, 10.1 mmol, 0.063 M as determined by HPLC calibration) was charged to a 250 mL round-bottom flask fitted with a distillation head. The solution was heated in an oil bath (70° C.) and the dichloromethane was removed by distillation until the internal temperature reached 60° C. (distillate temperature 34–40° C.). After cooling to room temperature, HCl (1 N, 140 mL, 140 mmol) and tert-butyl methyl ether (80 mL) were added and the resulting mixture was stirred for 10 minutes, until all solids were dissolved. The phases were separated and the aqueous layer was back-extracted with tert-butyl methyl ether (40 mL). The combined tert-butyl methyl ether layer was washed with HCl (1 N, 2×140 mL) and water (5×100 mL, pH of water washes; 0, 2, 4, 5, 6 respectively). The tert-butyl methyl ether layer was then extracted with a solution of tris(hydroxymethyl) aminomethane (2.58 g, 21.3 mmol) in water (20 mL). Acetone (70 mL) was added to the product rich aqueous layer until the solution turned cloudy, stirred at room temperature for 1.75 hours. Added acetone (20 mL) and stirred at room temperature for 16.5 hours, followed by addition of acetone (100 mL) over a period of 30 minutes. The resulting suspension was cooled to 0° C. and stirred for 2.5 hours. The solid was collected by filtration and washed with acetone (2×20 mL). The wet cake was dried under vacuum (25 mmHg) at room temperature for 21 hours to give the crystalline product, bis-[tris(hydroxymethyl) ammoniummethane] salt (5.08 g) as an acetone solvate (0.7 equivalent). $^1$H NMR: (300 MHz, DMSO-d$_6$) δ 7.88 (s, 1H), 7.69 (d, J=2.3, 1H), 7.49 (dd, J=2.6, 8.8, 1H), 7.41 (s, 1H), 7.04 (dd, J=1.2, 8.9, 1H), 5.40 (d, J=5.9, 2H), 5.25 (bs, 12H), 3.52 (s, 3H), 3.35 (s, 12H), 2.15 (s, 4.4H, acetone peak). $^{31}$P NMR: (300 MHz, DMSO-d$_6$) δ 0.11. $^{19}$F NMR: (500 MHz, DMSO-d$_6$) δ−67.9, −166.0.

What is claimed is:

1. A compound of the formula

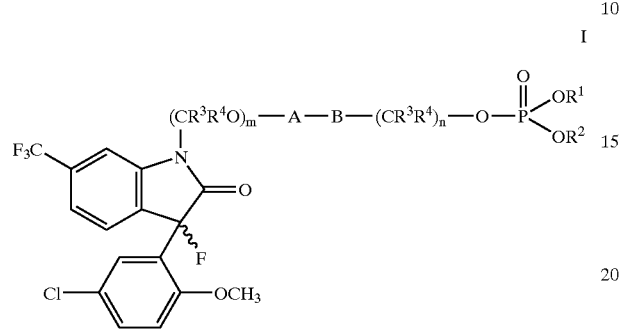

I wherein the wavy bond (∿) represents the racemate, the (R)-enantiomer or the (S)-enantiomer;

A is a direct bond or (C=O);

B is a direct bond, oxygen or nitrogen;

m is 0 or 1;

n is 1, 2 or 3;

$R^1$ and $R^2$ each are independently hydrogen, $C_{1-6}$ alkyl, benzyl, 4-methoxybenzyl, (lower)alkanoyloxy(lower)alkyl, (lower)alkoxycarbonyloxy(lower)alkyl, (lower)alkoxycarbonyl(lower)alkyl, (5-methyl-2-oxo-1,3-dioxol-4-yl)methyl or dihydroxypropyl; and when $R^1$ is hydrogen, $R^2$ may also be —P(O)OR$^5$OR$^6$ or heteroaryl;

$R^3$ and $R^4$ each are independently hydrogen or $C_{1-4}$ alkyl; and $R^5$ and $R^6$ each are independently hydrogen, $C_{1-6}$ alkyl, benzyl, 4-methoxybenzyl, (lower)alkanoyloxy(lower)alkyl, (lower)alkoxycarbonyloxy(lower)alkyl, (lower)alkoxycarbonyl(lower)alkyl, (5-methyl-2-oxo-1,3-dioxol-4-yl)methyl or dihydroxypropyl;

or a nontoxic pharmaceutically acceptable salt or solvate thereof.

2. The compound of claim 1 wherein the wavy bond (∿) represents the racemate, the (R)-enantiomer or the (S)-enantiomer; A is a direct bond or (C=O); B is a direct bond or oxygen; m is 0 or 1; n is 1, 2 or 3; $R^1$ and $R^2$ each are independently hydrogen, $C_{1-6}$ alkyl, benzyl, 4-methoxybenzyl, (lower)alkanoyloxy(lower)alkyl, (lower)alkoxycarbonyloxy(lower)alkyl, (lower)alkoxycarbonyl (lower)alkyl, (5-methyl-2-oxo-1,3-dioxol-4-yl)methyl or dihydroxypropyl; and when $R^1$ is hydrogen, $R^2$ may also be —P(O)OR$^5$OR$^6$; $R^3$ and $R^4$ each are independently hydrogen or $C_{1-4}$ alkyl; and $R^5$ and $R^6$ each are independently hydrogen, $C_{1-6}$ alkyl, benzyl, 4-methoxybenzyl, (lower)alkanoyloxy(lower)alkyl, (lower)alkoxycarbonyloxy(lower)alkyl, (lower)alkoxycarbonyl(lower)alkyl, (5-methyl-2-oxo-1,3-dioxol-4-yl)methyl or dihydroxypropyl; or a nontoxic pharmaceutically acceptable salt or solvate thereof.

3. The compound of claim 2 selected from the group consisting of:

(S)-phosphoric acid mono-[3-(5-chloro-2-methoxy-phenyl)-3-fluoro-2-oxo-6-trifluoromethyl-2,3-dihydro-indol-1-ylmethyl] ester;

(R)-phosphoric acid mono-[3-(5-chloro-2-methoxy-phenyl)-3-fluoro-2-oxo-6-trifluoromethyl-2,3-dihydro-indol-1-ylmethyl] ester;

(S)-3-(5-chloro-2-methoxy-phenyl)-3-fluoro-2-oxo-6-trifluoromethyl-2,3-dihydro-indole-1-carboxylic acid 2-phosphonooxy-propyl ester;

(S)-3-(5-chloro-2-methoxy-phenyl)-3-fluoro-2-oxo-6-trifluoromethyl-2,3-dihydro-indole-1-carboxylic acid 2-phosphonooxy-ethyl ester;

(S)-(2-phosphonooxy-ethyl)-carbamic acid 3-(5-chloro-2-methoxy-phenyl)-3-fluoro-2-oxo-6-trifluoromethyl-2,3-dihydro-indol-1-ylmethyl ester;

(S)-phosphonooxy-acetic acid 3-(5-chloro-2-methoxy-phenyl)-3-fluoro-2-oxo-6-trifluoromethyl-2,3-dihydro-indol-1-ylmethyl ester;

(S)-3-(5-chloro-2-methoxy-phenyl)-3-fluoro-2-oxo-6-trifluoromethyl-2,3-dihydro-indole-1-carboxylic acid phosphonooxymethyl ester;

(S)-3-phosphonooxy-propionic acid 3-(5-chloro-2-methoxy-phenyl)-3-fluoro-2-oxo-6-trifluoromethyl-2,3-dihydro-indol-1-ylmethyl ester;

(S)-pyrophosphoric acid [3-(5-chloro-2-methoxy-phenyl)-3-fluoro-2-oxo-6-trifluoro methyl-2,3-dihydro-indol-1-yl methyl ester;

(S)-phosphoric acid-[3-(5-chloro-2-methoxy-phenyl)-3-fluoro-2-oxo-6-trifluoromethyl-2,3-dihydro-indol-1-ylmethyl ester] methyl ester; and (S)-phosphoric acid-[3-(5-chloro-2-methoxy-phenyl)-3-fluoro-2-oxo-6-trifluoromethyl-2,3-dihydro-indol-1-ylmethyl ester] ethyl ester;

or a nontoxic pharmaceutically acceptable salt or solvate thereof.

4. The compound of claim 3 which is (S)-phosphoric acid mono-[3-(5-chloro-2-methoxy-phenyl)-3-fluoro-2-oxo-6-trifluoromethyl-2,3-dihydro-indol-1-ylmethyl] ester or a nontoxic pharmaceutically acceptable salt or solvate thereof.

5. The compound of claim 4 which is (S)-phosphoric acid mono-[3-(5-chloro-2-methoxy-phenyl)-3-fluoro-2-oxo-6-trifluoromethyl-2,3-dihydro-indol-1-ylmethyl] ester, bis[tris (hydroxymethyl)ammoniummethane] salt or solvate thereof.

6. A pharmaceutical composition comprising a therapeutically effective amount of a compound as defined in claim 1 in association with a pharmaceutically acceptable carrier or diluent.

7. A method for the treatment of disorders responsive to opening of the large conductance calcium-activated potassium channels in a mammal in need thereof, wherein said disorder is selected from the group consisting of ischemia, stroke, convulsions, epilepsy, asthma, irritable bowel syndrome, migraine, traumatic brain injury, elevated intracranial pressure, spinal cord injury, carbon monoxide poisoning, sexual dysfunction and urinary incontinence which comprises administering to said mammal a therapeutically effective amount of a compound as defined in claim 1.

8. The method of claim 7 wherein the disorder is stroke.

9. The method of claim 7 wherein the disorder is traumatic brain injury.

10. The method of claim 7 wherein the disorder is elevated intracranial pressure.

* * * * *